United States Patent
Yukita et al.

(10) Patent No.: US 11,253,341 B2
(45) Date of Patent: Feb. 22, 2022

(54) DENTAL COUPLING MEMBER, MOUTHPIECE, AND ORTHODONTIC TOOL

(71) Applicants: Mitsui Chemicals, Inc., Tokyo (JP); Takashima Sangyo Co., Ltd., Nagano (JP)

(72) Inventors: Takashi Yukita, Chiba (JP); Hideyuki Nagai, Iwakuni (JP); Yasufumi Tsuchiya, Funabashi (JP); Daigo Hama, Chino (JP); Kohei Yazaki, Suwa (JP); You Sato, Suwa (JP); Junji Oowa, Okaya (JP)

(73) Assignees: Mitsui Chemicals, Inc., Tokyo (JP); Takashima Sangyo Co., Ltd., Nagano (JP)

( * ) Notice: Subject to any disclaimer, the term of this patent is extended or adjusted under 35 U.S.C. 154(b) by 364 days.

(21) Appl. No.: 16/342,649

(22) PCT Filed: Oct. 12, 2017

(86) PCT No.: PCT/JP2017/036906
§ 371 (c)(1),
(2) Date: Apr. 17, 2019

(87) PCT Pub. No.: WO2018/074307
PCT Pub. Date: Apr. 26, 2018

(65) Prior Publication Data
US 2020/0046466 A1    Feb. 13, 2020

(30) Foreign Application Priority Data

Oct. 17, 2016 (JP) .............................. JP2016-203869
Nov. 8, 2016 (JP) .............................. JP2016-218139

(Continued)

(51) Int. Cl.
*A61C 7/36* (2006.01)
*A61C 7/08* (2006.01)
*A61C 7/10* (2006.01)

(52) U.S. Cl.
CPC .................. *A61C 7/36* (2013.01); *A61C 7/08* (2013.01); *A61C 7/10* (2013.01)

(58) Field of Classification Search
CPC .... A61C 7/00; A61C 7/06; A61C 7/08; A61C 7/10; A61C 7/36; F16B 35/02;
(Continued)

(56) References Cited

U.S. PATENT DOCUMENTS 1,370,198 A * 3/1921 Dillingham ............. F16B 35/02
411/306
1,638,165 A * 8/1927 Rau ......................... F16B 35/02
411/419

(Continued)

FOREIGN PATENT DOCUMENTS

FR    2952294 A1 *  5/2011  ............... A61C 7/36
JP    2002-512073 A    4/2002
(Continued)

OTHER PUBLICATIONS

Extended European Search Report dated Sep. 16, 2020.
International Search Report from International Application No. PCT/JP2017/036906 dated Dec. 19, 2017.

*Primary Examiner* — Edward Moran
*Assistant Examiner* — Matthew P Saunders
(74) *Attorney, Agent, or Firm* — Brundidge & Stanger, P.C.

(57) ABSTRACT

A dental coupling member related to a first aspect of the invention comprises: a rod having, at one end region, a first coupling part that is coupled to a first attachment part of a first dental tool, and having a screw part at the other end region; and a cylindrical body having, in an inner circum-
(Continued)

ferential surface of one end region, a screwed part into which the screw part is screwed, and having, at the other end region, a second coupling part that is coupled to a second attachment part of a second dental tool. This dental coupling member comprises a different-torque part at the screw part and/or the screwed part, the different-torque part having a different torque for screwing against the other of the screw part and the screwed part. This dental coupling member suppresses the occurrence of loosening between the screw part and the screwed part.

18 Claims, 23 Drawing Sheets

(30) Foreign Application Priority Data

Nov. 25, 2016 (JP) .............................. JP2016-228731
Nov. 25, 2016 (JP) .............................. JP2016-228732

(58) Field of Classification Search
CPC .. F16B 35/04; F16B 25/0057; F16B 25/0068; F16B 31/02; F61B 7/18
See application file for complete search history.

(56) References Cited

U.S. PATENT DOCUMENTS

| | | | | |
|---|---|---|---|---|
| 2,380,944 A | * | 8/1945 | Cole | F16B 39/30 411/308 |
| 5,429,014 A | * | 7/1995 | Laue | B21K 1/766 29/428 |
| 5,738,514 A | * | 4/1998 | DeVincenzo | A61C 7/36 433/18 |
| 5,755,543 A | * | 5/1998 | Culpen | F16B 35/02 411/419 |
| 5,879,157 A | * | 3/1999 | Scheu | A61C 7/36 433/19 |
| 5,919,042 A | | 7/1999 | Williams | |
| 6,012,920 A | * | 1/2000 | Woo | A61C 7/10 433/19 |
| 9,198,741 B2 | * | 12/2015 | Morin | A61C 7/36 |
| 2001/0053318 A1 | * | 12/2001 | Osame | F16B 35/02 411/419 |
| 2007/0224567 A1 | | 9/2007 | Robson | |
| 2008/0176185 A1 | * | 7/2008 | Williams | A61C 7/36 433/140 |
| 2010/0068003 A1 | * | 3/2010 | Wagner | B21H 3/02 411/386 |
| 2010/0239995 A1 | | 9/2010 | Williams | |
| 2014/0224257 A1 | * | 8/2014 | Abramson | A61F 5/566 128/848 |
| 2014/0230829 A1 | * | 8/2014 | Rogers | A61F 5/566 128/848 |

FOREIGN PATENT DOCUMENTS

| | | | | |
|---|---|---|---|---|
| JP | 2012-002324 A | | 1/2012 | |
| WO | 1998/018581 A1 | | 5/1998 | |
| WO | WO-9818581 | * | 5/1998 | |
| WO | WO-2019230152 A1 | * | 12/2019 | A61C 7/08 |

* cited by examiner

DENTAL COUPLING MEMBER, MOUTHPIECE, AND ORTHODONTIC TOOL

TECHNICAL FIELD

The techniques of the present application relate to dental coupling members, mouthpieces, and orthodontic appliances.

BACKGROUND ART

Dental mouthpieces have been used for treatment of sleep apnea syndrome, temporomandibular disorder and the like. For correcting a row of teeth, orthodontic appliances are used. As an example of such a mouthpiece, a dental appliance including a mandibular arch expander and a maxillary arch expander coupled to each other via a pair of adjustable connectors or Herbst appliances is disclosed in Patent Literature (hereinafter, abbreviated as PTL) 1, for instance.

CITATION LIST

Patent Literature

PTL 1
Japanese Unexamined Patent Application Publication (Translation of PCT Application) No. 2002-512073

SUMMARY OF INVENTION

Technical Problem

In the technique disclosed in PTL 1, the mandibular and maxillary arch expanders are coupled to one another by two nested Herbst assemblies. The two assemblies each include a rear pipe, a front pipe, and a rod piercing through the two pipes. A thread formed externally on the rear end of a hollow body of the rear pipe engages with a thread formed on the inner side of a front end of the hollow body of the front pipe, thus coupling the front pipe and the rear pipe by the threads.

For a structure that screws two screws (a screwing part and a screwed part) together to couple the members (a rod and a cylinder) bearing these screws with each other, such as described in PTL 1, it is desirable to maintain the relative positions of the members by restraining the screws from becoming loose. For a dental mouthpiece or orthodontic appliance in particular, it is desirable to maintain the relative positions of two dental appliances attached on the row of teeth of the upper jaw and the lower jaw.

In view of this fact, an object of the present invention according to a first aspect is to provide dental coupling members, mouthpieces and orthodontic appliances that restrain loosening between a screwing part and a screwed part.

Also, for a structure in which an insert is inserted into a tubular pipe (an outer tube), such as described in PTL 1, it is desirable to appropriately limit the range of insertion of the insert so that the insert is not excessively inserted relative to the outer tube. However, shaping of the outer tube is difficult with, for example, a structure that has portions with two distinct inner diameters formed inside the outer tube and uses the portion where the inner diameter changes as a wall to be contacted by the insert.

In view of this fact, an object of the present invention according to a second aspect is to provide dental coupling members, mouthpieces, and orthodontic appliances that can limit an excessive insertion of the insert into the outer tube with a simple structure.

Solution to Problem

A dental coupling member according to a first aspect of the present invention includes: a first elongated body including, in a first-orientation end region, a first coupling part to be coupled with a first attaching part of a first dental appliance and including a screwing part in a second-orientation end region; and a second elongated body including, in a second-orientation end region, a second coupling part to be coupled with a second attaching part of a second dental appliance and including, on an inner peripheral surface of a first-orientation end region, a screwed part with which the screwing part is screwed. The dental coupling member includes, on either one or both of the screwing part and the screwed part, a different-torque part that involves a different torque for screwing with another of the screwing part and the screwed part.

A dental coupling member according to a second aspect of the present invention includes: a first elongated body including, in a first-orientation end region, a first coupling part to be coupled with a first attaching part of a first dental appliance, and including a screwing part with at least two distinct outer diameters formed in a second-orientation end region; and a second elongated body including, in a second-orientation end region, a second coupling part to be coupled with a second attaching part of a second dental appliance and including a screwed part formed on an inner peripheral surface of a first-orientation end region, the screwed part being for screwing with the screwing part.

A mouthpiece of the present invention includes: any of the dental coupling members; a mandibular piece as the first dental appliance; and a maxillary piece as the second dental appliance.

An orthodontic appliance of the present invention includes: any of the dental coupling members described above; a lower-teeth attachment as the first dental appliance to be attached to lower teeth for orthodontically correcting a row of teeth; and an upper-teeth attachment as the second dental appliance to be attached to upper teeth for orthodontically correcting a row of teeth.

Advantageous Effects of Invention

In the first aspect, the present invention can restrain loosening between a screwing part and a screwed part.

In the second aspect, the present invention can limit an excessive insertion of the insert into the outer tube with a simple structure.

DESCRIPTION OF EMBODIMENTS

In the following description, a "first-orientation end region (a first-orientation axial end)" of an outer tube, an inner tube, or a rod, or an associated member (a male screw part, for example) is intended to indicate an end region and surroundings thereof in the same direction for all of these members. That is to say, the "first-orientation end region" means, for all of these members, either an axial end and surroundings thereof on the side of a mandibular dental appliance (a first dental appliance) when a dental coupling member is attached to a mouthpiece or orthodontic appliance, or an axial end and surroundings thereof on the side of a maxillary dental appliance (a second dental appliance) when the dental coupling member is attached to the mouthpiece or orthodontic appliance. A "second-orientation end region" means an end region and surroundings thereof on the opposite side to the "first-orientation end region" for all of these members. That is, the end region on the opposite side of the axial end and the surroundings thereof on the side of the maxillary dental appliance means the axial end and the surroundings thereof on the side of the mandibular dental appliance; and the end region on the opposite side of the axial end and the surroundings thereof on the side of the mandibular dental appliance means the axial end and the surroundings thereof on the side of the maxillary dental appliance.

Similarly, the "first-orientation end region side" of an outer tube, an inner tube, or a rod, or an associated member (a male screw part, for example) indicates the same direction on the side where the first-orientation end region is formed for all these members. That is, the "first-orientation end region side" means, with respect to all of these members, either the direction toward the side of the mandibular dental appliance (the first dental appliance) when the dental coupling member is attached to the mouthpiece or orthodontic appliance, or the direction toward the side of the maxillary dental appliance (the second dental appliance) when the dental coupling member is attached to the mouthpiece or orthodontic appliance. The "second-orientation end region side" means the direction toward the opposite side of the "first-orientation end region side" for all of these members.

In the following description, a male screw part (screwing part) or a female screw part (screwed part) being "rotationally symmetric" means that a projection of the same as seen in the direction of the axial center of the rod or the axial center of the inner tube is rotationally symmetric about the axial center.

In the following description, the "outer diameter" and "inner diameter" of a male screw part (screwing part) or a female screw part (screwed part) mean the distance between the vertices of opposing threads.

1. Basic Configuration 1-1. Mouthpiece

Figure 1:
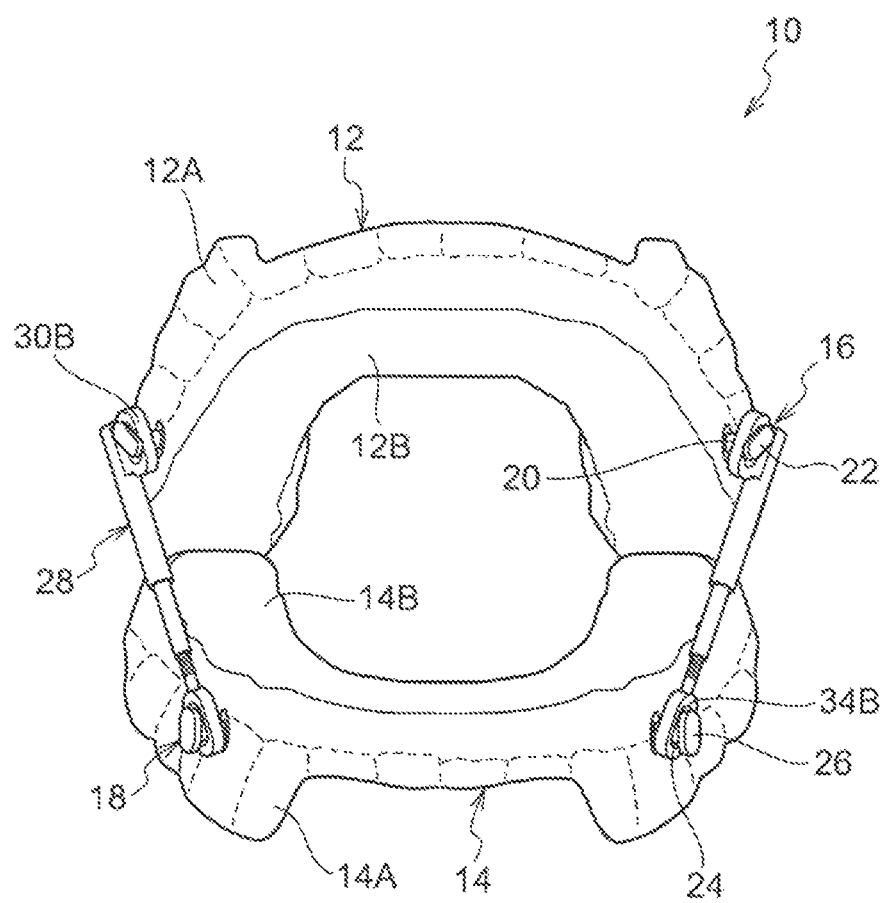
FIG. 1 is a front view showing a mouthpiece according to an exemplary embodiment of the present invention.

Mouthpiece 10 is a dental mouthpiece used for mitigation or prevention of snore, teeth grinding, apnea during sleep or the like. In an example, this mouthpiece 10 includes maxillary dental appliance (a second dental appliance) 12 to be worn on the upper jaw teeth and mandibular dental appliance (a first dental appliance) 14 to be worn on the lower jaw teeth as shown in FIG. 1.

Maxillary dental appliance 12 and mandibular dental appliance 14 may be made of, but not limited to, acrylic resin, for example. For example, maxillary dental appliance 12 and mandibular dental appliance 14 may be made of a single hard material having a flexural modulus of 2,000 MPa or more and 3,000 MPa or less or combination of a soft material with 10 MPa or more and 300 MPa or lower and a hard material with 1,000 MPa or more and 3,000 MPa or less.

Maxillary dental appliance 12 and mandibular dental appliance 14 may also be made of relatively soft material having a tensile strength of 150 N or more and less than 2,000 N, particularly 150 N or more and 500 N or less. In that case, maxillary dental appliance 12 and mandibular dental appliance 14 of mouthpiece 10 would have high conformity to the teeth when they are worn.

The tensile strength refers to the strength at which a mouthpiece (3-mm thick) fabricated with a Nissin standard model tears in a tensile testing conducted in the molar direction (backward on the row of teeth) with a hole 1.5 mm in diameter bored at the sixth tooth in the maxillary dental appliance or mandibular dental appliance of the mouthpiece.

Materials with a tensile strength of 150 N or more and less than 2,000 N include, for example, olefin-based resins, polyester-based resin, urethane-based resin, polyamide-based resin, and acrylic rubber resin, where the olefin-based resin is preferable inter alia.

An olefin-based resin is a polymer made by homopolymerization of olefin or a copolymer of olefin and another monomer. Olefin with a carbon number of 2 to 6 containing ethylene, propylene, butene, methylpentene, and hexene is preferred. The other monomer may be vinyl acetate, for example.

Preferably, the olefin-based resin is polyethylene (PE), polyethylene-based resin, polypropylene (PP), polypropylene-based resin, and ethylene-vinyl acetate copolymer (EVA), for example, and more preferably, is polyethylene (PE), polyethylene-based resin, polypropylene (PP), or polypropylene-based resin.

Polyester-based resin is a polycondensate of polyvalent carboxylic acid (dicarboxylic acid) and polyalcohol (diol), for example, polyethyleneterephthalate (PET). Urethane-based resin is a polycondensate of a compound having an isocyanate group and a compound having a hydroxy group, for example, is thermoplastic polyurethane (TPU).

Polyamide-based resin is a polymer formed by binding of many monomers by amide bond, for example, nylon, para-amide, and meta-amide. Acrylic rubber resin consists mainly of acrylic rubber, for example, is a block copolymer of methyl methacrylate and butyl acrylate.

Material with a tensile strength of 150 N or more and less than 2,000 N may be a commercially available material, such as F327, a polypropylene resin manufactured by Prime Polymer Co., Ltd.

Maxillary dental appliance 12 is provided with upper attaching part (a second attaching part) 16 on outer wall surface 12A so as to project from outer wall surface 12A at the back on each of the right and left sides (the sixth or seventh tooth in FIG. 1), when seen from the center of the row of teeth. Upper attaching part 16 is made of metal.

Likewise, mandibular dental appliance 14 is provided with lower attaching part (a first attaching part) 18 on outer wall surface 14A so as to project from outer wall surface 14A at the back on each of the right and left sides (the third or fourth tooth in FIG. 1), when seen from the center of the row of teeth. Lower attaching part 18 is made of metal.

Figure 2A:
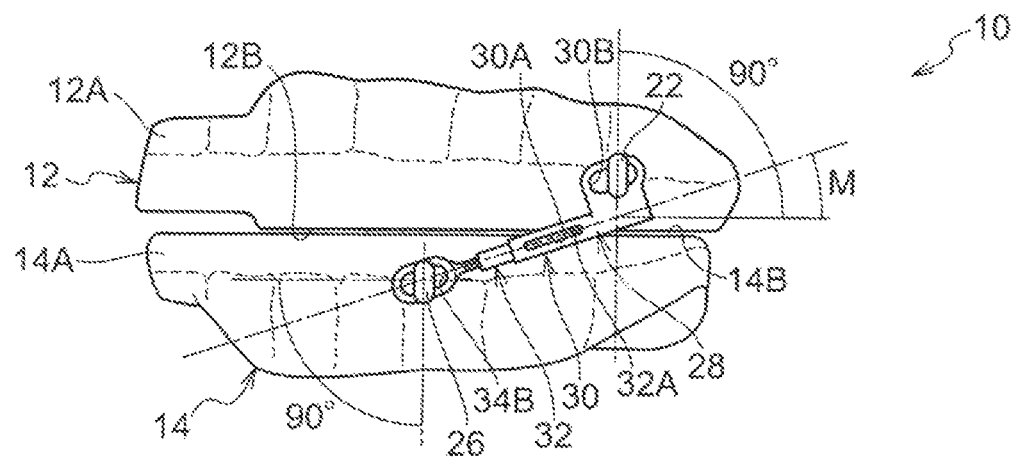
FIG. 2A is a side view showing the state of the mouthpiece when the mouth is closed.

Upper attaching part 16 has columnar shaft 20 with one end fixed to outer wall surface 12A of maxillary dental appliance 12, and a flange 22 provided at the other end (a tip) of shaft 20. Flange 22 is of a corner-rounded rectangular shape with a major axis and a minor axis. As shown in FIG. 2A, the angle of the major axis of flange 22 relative to opposing surface 12B of maxillary dental appliance 12 which faces mandibular dental appliance 14 is about 90 degrees.

Similarly, lower attaching part 18 has columnar shaft 24 with one end fixed on outer wall surface 14A of mandibular dental appliance 14, and flange 26 of a corner-rounded rectangular shape provided at the tip of shaft 24. As shown in FIG. 2A, the angle of the major axis of flange 26 relative to opposing surface 14B of mandibular dental appliance 14 which faces maxillary dental appliance 12 is about 90 degrees. The angle of the major axis of flange 22 relative to opposing surface 12B and the angle of the major axis of flange 26 relative to opposing surface 14B may both be any angle outside the range of 10 to 60 degrees.

Right upper attaching part 16 and right lower attaching part 18 have dental coupling member 28 made of metal attached thereon, while left upper attaching part 16 and left lower attaching part 18 have another dental coupling member 28 made of metal attached thereon. Dental coupling member 28 is rotatable about the axis of upper attaching part 16 when coupled to upper attaching part 16 and is also rotatable about the axis of lower attaching part 18 when coupled to lower attaching part 18. Dental coupling member 28 couples maxillary dental appliance 12 and mandibular dental appliance 14 with each other in an openable and closable manner and positions them so that mandibular dental appliance 14 does not move backward on the row of teeth relative to maxillary dental appliance 12.

In mouthpiece 10, when seen from the center of the row of teeth, upper attaching part 16 is situated on the back side with respect to lower attaching part 18 (on the back teeth side). That is, mouthpiece 10 is of Push type: it pushes mandibular dental appliance 14 (the lower jaw) frontward by means of dental coupling member 28 when mouthpiece 10 is worn.

1-2. Dental Coupling Member

Figure 3A:
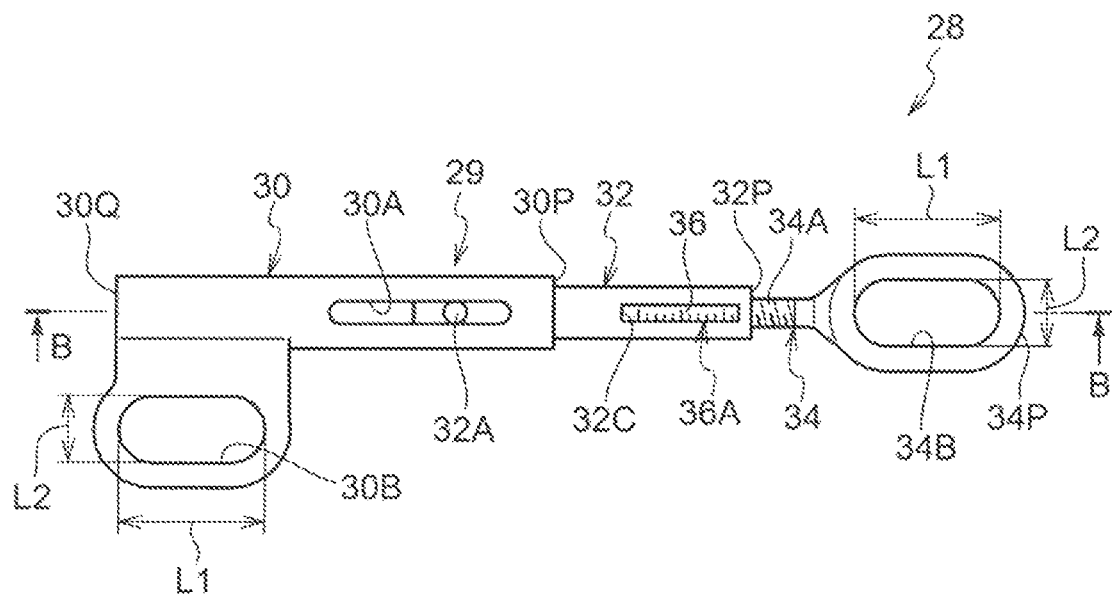
FIG. 3A is a plan view showing an exemplary dental coupling member according to the present invention.
Figure 3B:
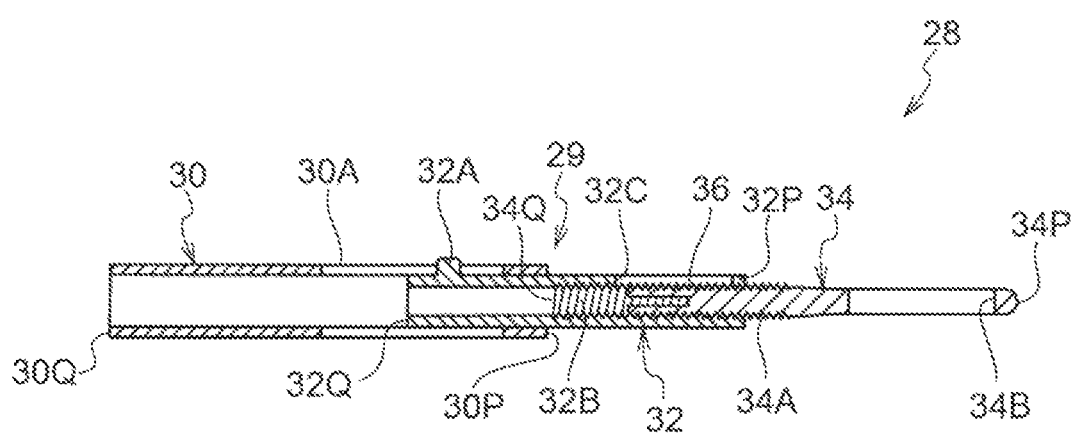
FIG. 3B is a cross-sectional view taken along line B-B in FIG. 3A.

FIGS. 3A and 3B show an exemplary dental coupling member 28 for attachment to mouthpiece 10. Dental coupling member 28 has cylinder 29, which is an elongated body. As shown in FIGS. 3A and 3B, cylinder 29 has tubular outer tube 30 being open at the end on first-orientation end region 30P side and at the end on second-orientation end region 30Q side, and tubular inner tube 32 slidably inserted in outer tube 30. Dental coupling member 28 further has rod 34, which is an elongated body to be inserted into inner tube 32 (cylinder 29).

Long hole 30A is formed in the outer peripheral surface of outer tube 30 between first-orientation end region 30P and second-orientation end region 30Q along the axial direction. At a position offset from the axial center of second-orientation end region 30Q of outer tube 30, upper eyelet 30B of a corner-rounded rectangular shape to be engaged with flange 22 of upper attaching part 16 in FIG. 1 is formed. Upper eyelet 30B is of a similar shape to flange 22 (a corner-rounded rectangular shape with a longer diameter and a shorter diameter) and is located such that the direction of the longer diameter is the same as the longitudinal direction of dental coupling member 28 (the axial direction of outer tube 30).

Upper eyelet 30B is formed with a size slightly larger than flange 22. Specifically, a length L1 of the longer diameter of upper eyelet 30B is greater than a length R1 of the major axis of flange 22 shown in FIG. 2B.

Figure 2B:
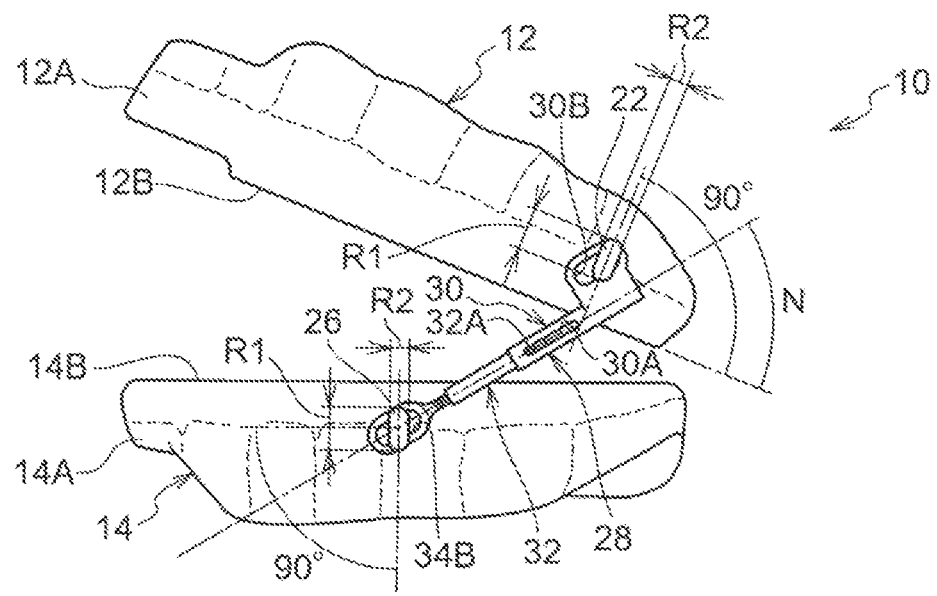
FIG. 2B is a side view showing the state of the mouthpiece when the mouth is open.

Meanwhile, a length L2 of the shorter diameter of upper eyelet 30B is greater than a length R2 of the minor axis of flange 22 shown in FIG. 2B and is shorter than the length R1 of the major axis of flange 22. This allows upper eyelet 30B to be attached to and detached from flange 22 only at a position where the direction of its longer diameter is aligned with the direction of the major axis of flange 22.

Housed part 32A, which is a protrusion, is formed so as to project on the outer peripheral surface of second-orientation end region 32Q of inner tube 32. Housed part 32A has a diameter smaller than the width of long hole 30A of outer tube 30, and is slidably inserted into and housed in long hole 30A such that housed part 32A also slides in long hole 30A upon sliding of inner tube 32 in outer tube 30. On the inner peripheral surface of first-orientation end region 32P of inner tube 32, female screw part 32B is formed. On the outer peripheral surface of inner tube 32 near first-orientation end region 32P, opening 32C is formed.

In second-orientation end region 34Q of rod 34, male screw part 34A to be screwed with female screw part 32B of inner tube 32 is formed. Non-threaded part 36 is provided as a part of male screw part 34A along the axial direction, with scale 36A formed on non-threaded part 36.

In first-orientation end region 34P of rod 34, lower eyelet 34B of a corner-rounded rectangular shape to be engaged with flange 26 of lower attaching part 18 in FIG. 1 is formed on an axial center RA of rod 34. Lower eyelet 34B is of a similar shape to flange 26 (a corner-rounded rectangular shape with a longer diameter and a shorter diameter), with the direction of its longer diameter being the same as the longitudinal direction of dental coupling member 28 (the axial direction of rod 34).

As with upper eyelet 30B, lower eyelet 34B is formed with a size slightly larger than flange 26. Specifically, the length L1 of the longer diameter of lower eyelet 34B is longer than the length R1 of the major axis of flange 26 shown in FIG. 2B.

Meanwhile, the length L2 of the shorter diameter of lower eyelet 34B is greater than the length R2 of the minor axis of flange 26 shown in FIG. 2B and is shorter than the length R1 of the major axis of flange 26. This allows lower eyelet 34B to be attached to and detached from flange 26 only at a position where the direction of its longer diameter is aligned with the direction of the major axis of flange 26.

The length of dental coupling member 28 is steplessly adjusted by rotating rod 34 about the axis to adjust the amount of screwing of male screw part 34A into female screw part 32B of inner tube 32. Dental coupling member 28 also follows the motion of maxillary dental appliance 12 and mandibular dental appliance 14 by the sliding of inner tube 32 in outer tube 30.

In doing so, the sliding of inner tube 32 in both axial directions is limited by abutment of housed part 32A of inner tube 32 against the opposite ends (the right and left ends in FIG. 3A) of long hole 30A on outer tube 30. The distance (center-to-center distance) between upper attaching part 16 and lower attaching part 18 is typically adjusted between about 18 mm and 50 mm with dental coupling member 28.

1-3. Operation and Effect

As shown in FIG. 1, exemplary mouthpiece 10 is attached to a row of teeth by upper eyelet 30B catching on shaft 20 and lower eyelet 34B catching on shaft 24 such that maxillary dental appliance 12 and mandibular dental appliance 14 are coupled to each other by dental coupling member 28.

Here, by adjusting the amount of screwing of male screw part 34A into female screw part 32B in FIGS. 3A and 3B, the position of mandibular dental appliance 14 is adjusted so that mandibular dental appliance 14 does not lie on the back side on the row of teeth with respect to maxillary dental appliance 12. Mouthpiece 10 allows scale 36A formed on non-threaded part 36 of rod 34 to be viewed from opening 32C of inner tube 32. Thus, when male screw part 34A of rod 34 is screwed with female screw part 32B of inner tube 32, the amount of screwing of male screw part 34A can be checked by viewing scale 36A formed on non-threaded part 36 of rod 34 from opening 32C of inner tube 32.

In addition, when the mouth is closed, mouthpiece 10 limits the backward movement of mandibular dental appliance 14 on the row of teeth (to the right side in FIG. 3A) by the abutment of housed part 32A of inner tube 32 against the upper end (the right end in FIG. 3A) of long hole 30A in outer tube 30, as shown in FIG. 2A.

In mouthpiece 10, when the mouth is closed, an attachment angle M of dental coupling member 28, namely the angle of the longer diameter of upper eyelet 30B relative to opposing surface 12B of maxillary dental appliance 12 and the angle of the longer diameter of lower eyelet 34B relative to opposing surface 14B of mandibular dental appliance 14, is about 10 degrees.

Since the angle of the major axis of flange 22, 26 relative to opposing surface 12B or opposing surface 14B is about 90 degrees, the angle of the major axis of flange 22, 26 does not coincide with the angle of the longer diameter of upper eyelet 30B and lower eyelet 34B, respectively.

As a result, when the mouth is closed, passage of upper eyelet 30B and lower eyelet 34B through flange 22, 26 is substantially impossible. That is, it is substantially impossible to remove dental coupling member 28 from upper attaching part 16 and from lower attaching part 18, so that the coupled state between maxillary dental appliance 12 and mandibular dental appliance 14 is maintained.

Similarly, in mouthpiece 10, when the mouth is open, an attachment angle N of dental coupling member 28, namely the angle of the longer diameter of upper eyelet 30B relative to opposing surface 12B of maxillary dental appliance 12 and the angle of the longer diameter of lower eyelet 34B relative to opposing surface 14B of mandibular dental appliance 14, is about 40 to 60 degrees, as shown in FIG. 2B.

Since the angle of the major axis of flange 22, 26 relative to opposing surface 12B or opposing surface 14B is about 90 degrees, the angle of the major axis of flange 22, 26 does not coincide with the angle of the longer diameter of upper eyelet 30B and lower eyelet 34B, respectively.

As a result, passage of upper eyelet 30B and lower eyelet 34B through flange 22, 26 is also substantially impossible when the mouth is open. That is, it is substantially impossible to remove dental coupling member 28 from upper attaching part 16 and from lower attaching part 18, so that the coupled state between maxillary dental appliance 12 and mandibular dental appliance 14 is maintained.

When the mouth is open, dental coupling member 28 follows the motion of maxillary dental appliance 12 and mandibular dental appliance 14 by the sliding of inner tube 32 in outer tube 30. In doing so, housed part 32A of inner tube 32 moves downward from the upper end of long hole 30A of outer tube 30 (to the left side in FIG. 3B) to abut against the lower end of long hole 30A (the left end in FIG. 3B).

Figure 2C:
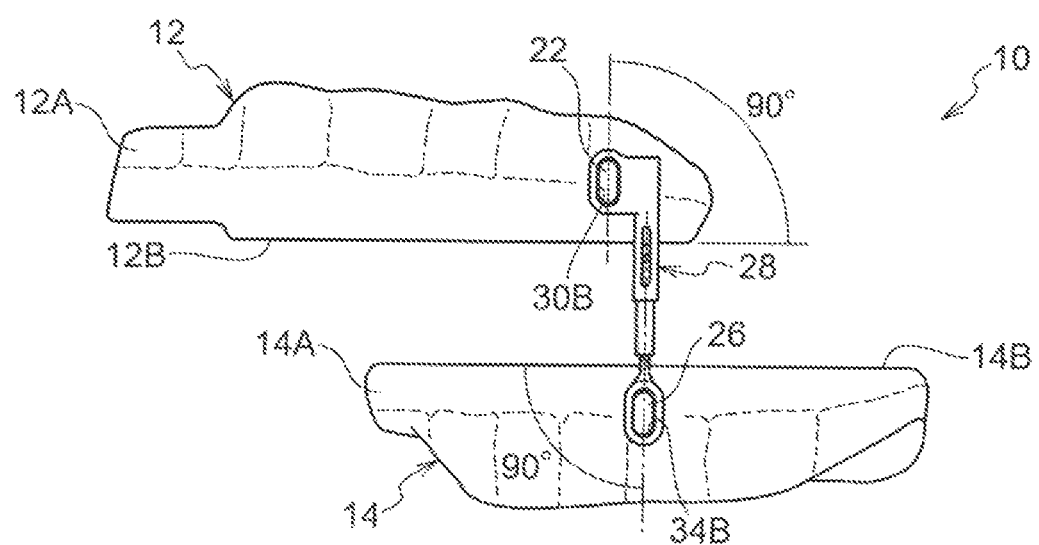
FIG. 2C is a side view showing the state of the mouthpiece when a dental coupling member is to be removed.

To attach or detach dental coupling member 28 to/from maxillary dental appliance 12 and mandibular dental appliance 14 (upper attaching part 16 and lower attaching part 18), mouthpiece 10 is first removed from the row of teeth. Then, as shown in FIG. 2C, maxillary dental appliance 12 and mandibular dental appliance 14 are separated from each other substantially in the horizontal direction so that the attachment angle of dental coupling member 28 becomes about 90 degrees.

Then, the angle of the longer diameter of upper eyelet 30B relative to opposing surface 12B of maxillary dental appliance 12 as well as the angle of the longer diameter of lower eyelet 34B relative to opposing surface 14B of mandibular dental appliance 14 also become about 90 degrees.

That is, the angle of the major axis of flange 22, 26 coincides with the angle of the longer diameter of upper eyelet 30B and lower eyelet 34B, respectively, allowing upper eyelet 30B and lower eyelet 34B to pass through flange 22, 26. Thus, dental coupling member 28 can be removed from upper attaching part 16 and lower attaching part 18.

Mouthpiece 10 allows the amount of screwing of male screw part 34A into female screw part 32B to be adjusted by rotation of rod 34 about the axis. Here, when lower eyelet 34B is engaged with flange 26, it is substantially impossible for rod 34 to rotate about the axis. This can prevent rod 34 from rotating to cause an unnecessary change in the length of dental coupling member 28 when mouthpiece 10 is worn on the row of teeth.

Mouthpiece 10 also limits the sliding of inner tube 32 in both axial directions by making housed part 32A of inner tube 32 provided in outer tube 30 abut against the opposite ends of long hole 30A formed between the opposite axial ends of outer tube 30.

This can make dental coupling member 28 and mouthpiece 10 compact in size compared to a configuration providing a member like a nut outside of outer tube 30 or a configuration that makes inner tube 32 and/or rod 34 abut against an outer end of outer tube 30.

Housed part 32A of inner tube 32 moves within long hole 30A of outer tube 30 in the axial direction. This can restrain inner tube 32 from rotating about the axis relative to outer tube 30 when it slides in outer tube 30.

Mouthpiece 10 also has flanges 22, 26 of a corner-rounded rectangular shape at upper attaching part 16 and lower attaching part 18, with upper eyelet 30B and lower eyelet 34B of dental coupling member 28 being of a corner-rounded rectangular shape slightly larger than flange 22, 26 (a similar shape).

Further, the angle of the major axis of flange 22, 26 relative to opposing surface 12B, 14B of maxillary dental appliance 12 or mandibular dental appliance 14 is about 90 degrees, which falls outside the attachment angle of dental coupling member 28.

Thus, when mouthpiece 10 is worn on the row of teeth, upper eyelet 30B and lower eyelet 34B are restrained to an extent that makes attachment and detachment to/from flange 22, 26 substantially impossible, allowing the coupled state between maxillary dental appliance 12 and mandibular dental appliance 14 to be maintained.

In contrast, when mouthpiece 10 is not worn on the row of teeth, upper eyelet 30B and lower eyelet 34B can be easily attached and detached to/from flange 22, 26. That is, just by changing the attachment angle relative to mouthpiece 10, dental coupling member 28 can be switched between a state facilitating attachment/detachment and a state restraining attachment/detachment.

Thus, maxillary dental appliance 12 and mandibular dental appliance 14 can be easily decoupled for maintenance or replacement, compared to a configuration with upper eyelet 30B and lower eyelet 34B being bonded, screwed or the like with flange 22, 26.

Additionally, since upper eyelet 30B and lower eyelet 34B have a corner-rounded rectangular shape, space is formed between shaft 20 of upper attaching part 16 and upper eyelet 30B and between shaft 24 of lower attaching part 18 and lower eyelet 34B when mouthpiece 10 is worn on the row of teeth. Sliding of shaft 20, 24 in this space enables dental coupling member 28 to follow the motion of maxillary dental appliance 12 and mandibular dental appliance 14 to an increased degree.

2. Embodiments

In the following, Embodiments 1 through 19 as variations of the dental coupling member are described. Embodiments 1 through 12 are examples of dental coupling members for restraining the loosening between the screwing part and the screwed part according to the first aspect of the present invention; Embodiments 13 through 16 are embodiments that can be applied to any of Embodiments 1 through 12 in combination as further variations of these embodiments; and Embodiments 17 through 19 are examples of dental coupling members for limiting an excessive insertion of the insert into the outer tube with a simple structure according to the second aspect of the present invention. In the description of the embodiments that follow, descriptions on features that overlap ones from previous embodiments and the associated operation or effect are omitted, and reference may be made as appropriate to the description of previous embodiments in which such features were described.

In Embodiments 1 through 12 according to the first aspect of the present invention, either one or both of male screw part 34A and female screw part 32B is provided with a different-torque part that involves a different torque for screwing with the other of male screw part 34A and female screw part 32B so as to form a portion with larger frictional force, thus restraining the loosening of male screw part 34A relative to female screw part 32B even after torque has been released.

2-1. Embodiment 1

Figure 4A:
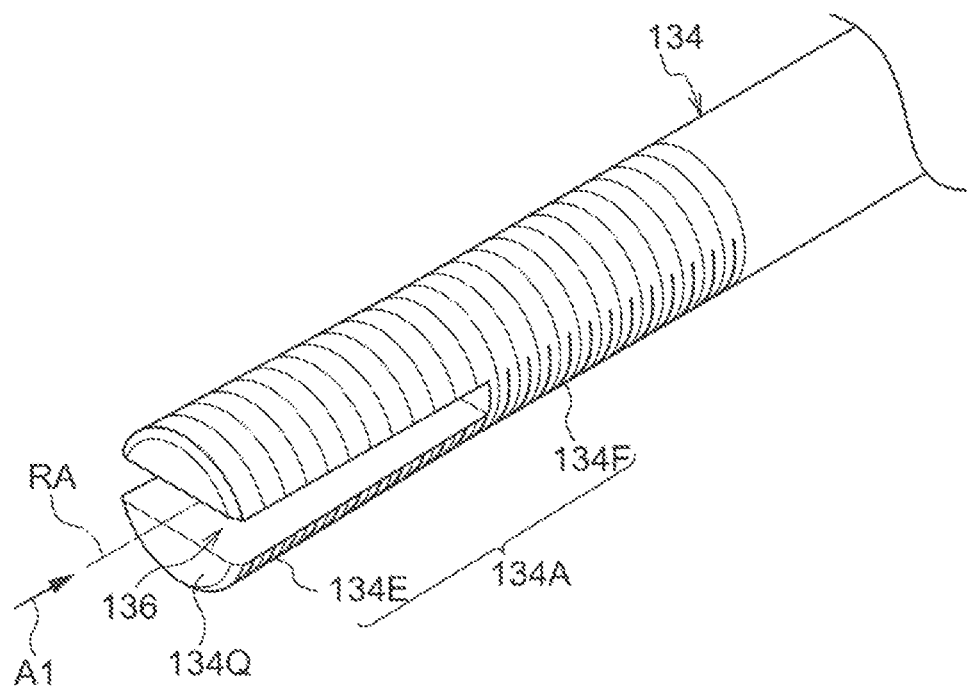
FIG. 4A is an enlarged perspective view showing a second-orientation end region of a rod of the dental coupling member according to Embodiment 1.
Figure 4B:
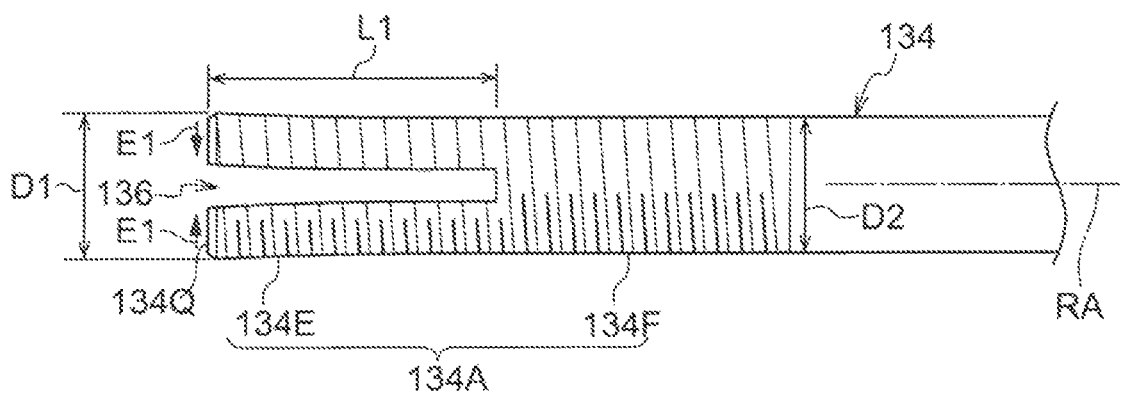
FIG. 4B is an enlarged side view showing the second-orientation end region of the rod of the dental coupling member according to Embodiment 1.

The dental coupling member according to Embodiment 1 has rod 134 shown in FIGS. 4A and 4B. As shown in FIGS. 4A and 4B, gap part 136 is formed in rod 134 on second-orientation end region 134Q side. Gap part 136 partially segments second-orientation end region 134Q of male screw part 134A in the direction orthogonal to the axial center RA (in the direction from the viewer's side into the page in FIG. 4B). In Embodiment 1, gap part 136 is a substantially cuboid slit that passes through the axial center RA of rod 134. In other words, gap part 136 is a slit extending from the axial center RA of rod 134 toward the outer periphery so as to segment male screw part 134A (into two). Consequently, in rod 134, second-orientation end region 134Q of male screw part 134A is segmented by gap part 136 into two parts that are substantially symmetric in the vertical direction in FIG. 4B. The two segment parts are substantially rotationally symmetric (substantially two-fold symmetric) by an angle of 180 degrees about the axial center RA. In the example shown in FIG. 4B, the length L1 (depth) of gap part 136 is such a length that reaches an intermediate position on male screw part 134A in the direction of axial center RA.

In this vertically segmented portion of male screw part 134A, increased diameter part 134E with an outer diameter increased by gap part 136 is formed. An outer diameter D1 of increased diameter part 134E (the vertical dimension in FIG. 4B) gradually increases toward second-orientation end region 134Q side. As opposed to this, of male screw part 134A, the portion where gap part 136 is not formed is constant diameter part 134F having a constant outer diameter D2. That is, male screw part 134A includes constant diameter part 134F having the constant outer diameter D2 and increased diameter part 134E having the outer diameter D1 greater than that of constant diameter part 134F. Increased diameter part 134E is an example of "large diameter part", constant diameter part 134F is an example of "small diameter part", and increased diameter part 134E and constant diameter part 134F are examples of "different-torque part" and of "different-diameter part".

Increased diameter part 134E can be formed, for example, by forming gap part 136 during the manufacture of rod 134 and then slightly spreading the vertically segmented portions away from each other. Due to the formation of gap part 136, increased diameter part 134E is elastically deformable in the direction toward the axial center RA of rod 134 (in the direction of arrow E1).

The outer diameter D1 at the tip of increased diameter part 134E is sized to be screwed with female screw part 32B of inner tube 32 with increased diameter part 134E elastically deformed in such a manner. In contrast, constant diameter part 134F has the outer diameter D2 smaller than that of increased diameter part 134E as mentioned above but is sized to be screwed with female screw part 32B of inner tube 32.

When male screw part 134A is screwed with female screw part 32B, male screw part 134A makes stronger contact with female screw part 32B and generates larger frictional force against female screw part 32B during rotation in increased diameter part 134E than in constant diameter part 134F. That is, large torque is required for rotation during screwing with female screw part 32B compared to a male screw part of a structure without increased diameter part 134E.

Inner tube 32 has a constant inner diameter in female screw part 32B. In other words, there is no portion where the inner diameter of the inner peripheral surface of inner tube 32 changes. Thus, inner tube 32 is of a shape that facilitates the formation of female screw part 32B.

With rod 134 of Embodiment 1, male screw part 134A includes increased diameter part 134E and constant diameter part 134F. Due to the formation of increased diameter part 134E, large torque is required when male screw part 134A is threaded into and rotated in female screw part 32B, compared with a rod having a male screw part with no formation of increased diameter part 134E. Accordingly, male screw part 134A is restrained from becoming loose relative to female screw part 32B even after the amount of screwing of male screw part 134A is adjusted, that is, after torque on rod 134 has been released. This restrains a shift in the relative position between rod 134 and inner tube 32. In turn, the position of mandibular dental appliance 14 relative to maxillary dental appliance 12 can be reliably maintained at the adjusted position as well.

In other words, increased diameter part 134E or the larger diameter portion tends to make strong contact with female screw part 32B of cylinder 29 and causes large frictional force compared to constant diameter part 134F or the smaller diameter portion, so that loosening of male screw part 134A relative to female screw part 32B can be restrained. In addition, since male screw part 134A is screwed with female screw part 32B also at constant diameter part 134F, force that acts in the state of being screwed with female screw part 32B is distributed throughout male screw part 134A, which can further restrain the loosening of male screw part 134A relative to female screw part 32B.

Further, increased diameter part 134E can elastically deform inward in the radial direction of rod 134 such that gap part 136 becomes smaller. That is, as increased diameter part 134E is screwed with female screw part 32B while undergoing elastic deformation, load can be made to act from increased diameter part 134E to female screw part 32B while restraining the abrasion of increased diameter part 134E.

In addition, due to a slit shape, gap part 136 is easy to form.

2-2. Embodiment 2

Figure 5:
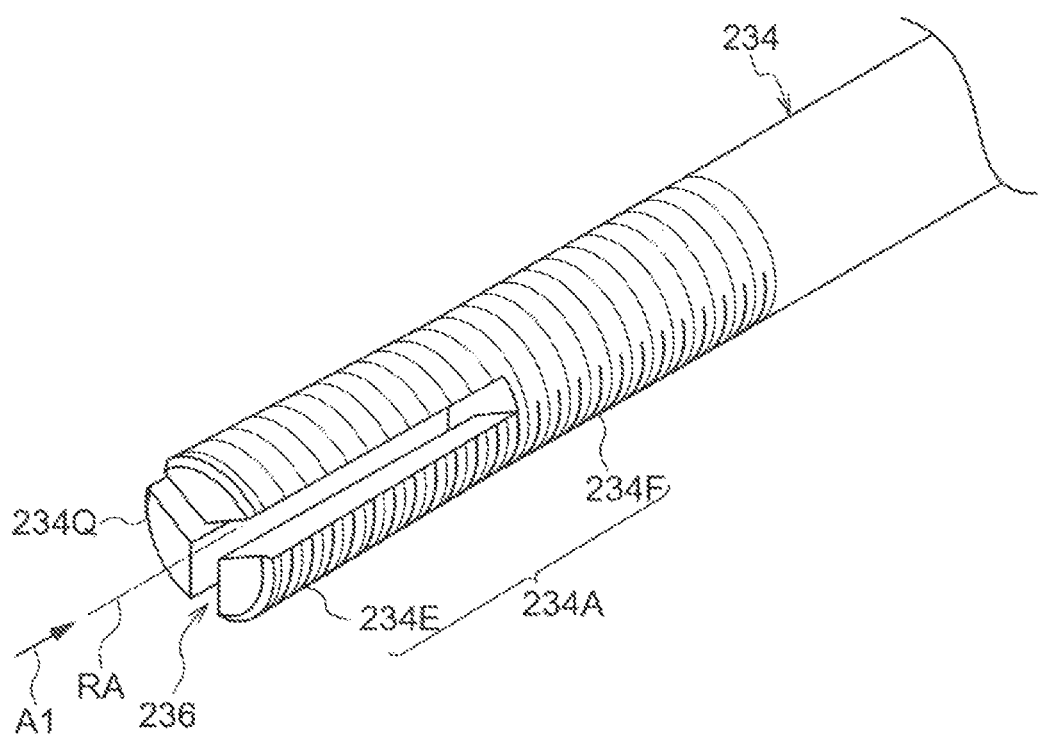
FIG. 5 is an enlarged perspective view showing the second-orientation end region of the rod of the dental coupling member according to Embodiment 2.

The dental coupling member according to Embodiment 2 has rod 234 shown in FIG. 5. This rod 234 has gap part 236 formed in second-orientation end region 234Q of male screw part 234A. When seen in the axial direction of rod 234 (in the direction of arrow A1), gap part 236 is formed in three parts toward the outer periphery side radially about the axial center RA of rod 234. In other words, gap part 236 is a slit extending toward the outer periphery from the axial center RA of rod 234 so as to segment male screw part 234A (into three). That is, a portion of male screw part 234A is segmented into three parts in the axial direction about the axial center RA. The three segment parts are substantially rotationally symmetric (substantially three-fold symmetric) by an angle of 120 degrees about the axial center RA.

Also in Embodiment 2, male screw part 234A includes increased diameter part 234E and constant diameter part 234F. Meanwhile, inner tube 32 also has a constant inner diameter in female screw part 32B in Embodiment 2. In Embodiment 2, accordingly, large torque is required when male screw part 234A is threaded into and rotated in female screw part 32B, compared to a rod having a male screw part with no formation of increased diameter part 234E. After the amount of screwing of male screw part 234A is adjusted, male screw part 234A is restrained from becoming loose relative to female screw part 32B. Increased diameter part 234E is an example of "large diameter part", constant diameter part 234F is an example of "small diameter part", and increased diameter part 234E and constant diameter part 234F are examples of "different-torque part" and of "different-diameter part".

In Embodiment 2, three segment parts are formed in second-orientation end region 234Q of male screw part 234A of rod 234, providing more segment parts than in Embodiment 1, in which two segment parts are formed. Such an increase in the number of segment parts results in a smaller size of each segment part, which makes it easier to bend the segment parts radially outward and thus facilitates the formation of increased diameter part 234E. On the other hand, a structure with a small number of segment parts facilitates processing or shaping of the rod because less gap parts are required. The number of segment regions in Embodiment 2 may be any number greater than two, such as four (substantially four-fold symmetric) or six (substantially six-fold symmetric). In other words, gap part 236 may be a slit of any form that segments second-orientation end region 234Q of male screw part 234A of rod 234 into substantially rotationally symmetric shapes of substantially three-fold or higher rotational symmetry.

2-3. Embodiment 3

Figure 6:
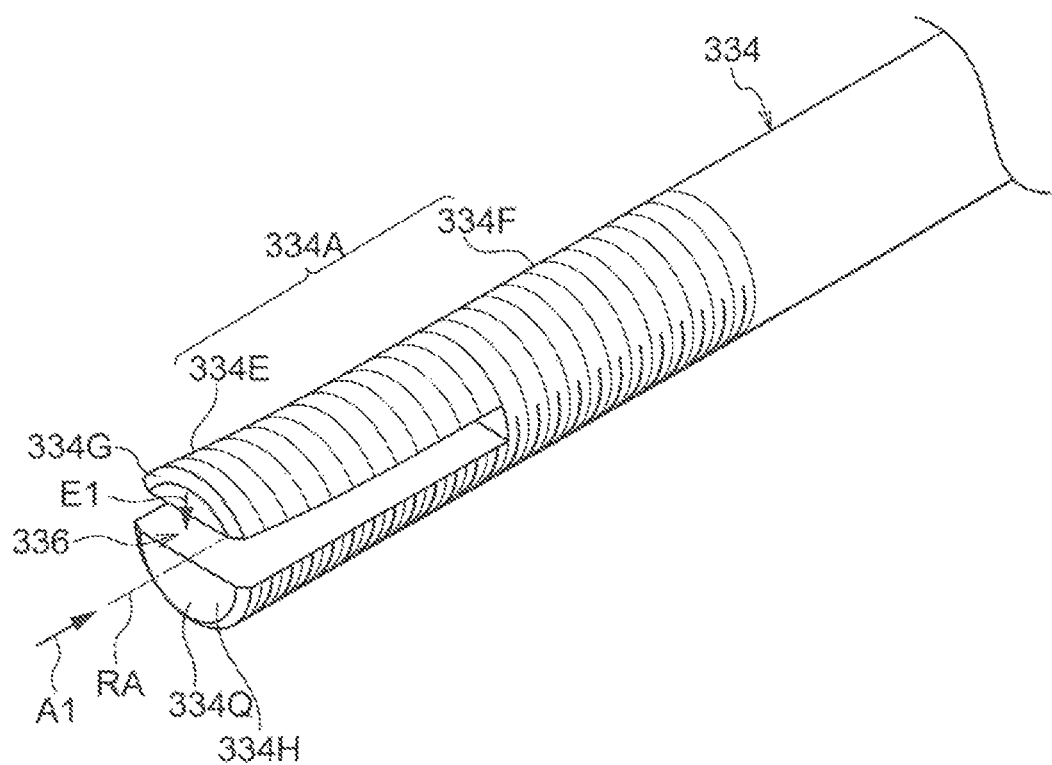
FIG. 6 is an enlarged perspective view showing the second-orientation end region of the rod of the dental coupling member according to Embodiment 3.

The dental coupling member according to Embodiment 3 has rod 334 shown in FIG. 6. This rod 334 has gap part 336 formed in second-orientation end region 334Q. Gap part 336 is a slit which is formed at a position offset from the axial center RA of rod 334, avoiding the axial center RA. Thus, increased diameter part 334E is segmented into shapes that are not rotationally symmetric, including a relatively small segment (small segment 334G) and a relatively large segment (large segment 334H), as seen from second-orientation end region 334Q side (in the direction of arrow A1). In other words, gap part 336 is a slit that segments male screw part 334A into a portion including the axial center RA of rod 334 and a portion not including the axial center RA of rod 334 (into two). Small segment 334G is easier to deform radially outward (in the direction opposite to arrow E1) than large segment 334H. Accordingly, increased diameter part 334E of rod 334 is virtually formed by the radially outward spreading of small segment 334G However, large segment 334H may also assume a shape spreading outward radially.

Also in Embodiment 3, male screw part 334A includes increased diameter part 334E and constant diameter part 334E Meanwhile, inner tube 32 has a constant inner diameter in female screw part 32B also in Embodiment 3. Accordingly, large torque is required when male screw part 334A is threaded into and rotated in female screw part 32B, compared to a rod having a male screw part with no formation of increased diameter part 334E. After the amount of screwing of male screw part 334A is adjusted, male screw part 334A is restrained from becoming loose relative to female screw part 32B. Increased diameter part 334E is an example of "large diameter part", constant diameter part 334F is an example of "small diameter part", and increased diameter part 334E and constant diameter part 334F are examples of "different-torque part" and of "different-diameter part".

In Embodiment 3, small segment 334G and large segment 334H are formed, with small segment 334G being easier to deform radially outward than large segment 334H. That is, elastic adjustment of the outer diameter D1 (not shown in FIG. 6, see FIG. 4B) at increased diameter part 334E of rod 334 is facilitated compared to a structure having segments 34D of a substantially rotationally symmetric shape, such as in Embodiment 1, and it is also possible to adjust frictional force when screwing increased diameter part 334E with female screw part 32B. Although second-orientation end region 334Q of male screw part 334A of rod 334 is segmented into two segment regions in FIG. 6, it may be segmented into three or more segment regions different in shape or size.

2-4. Embodiment 4

Figure 7A:
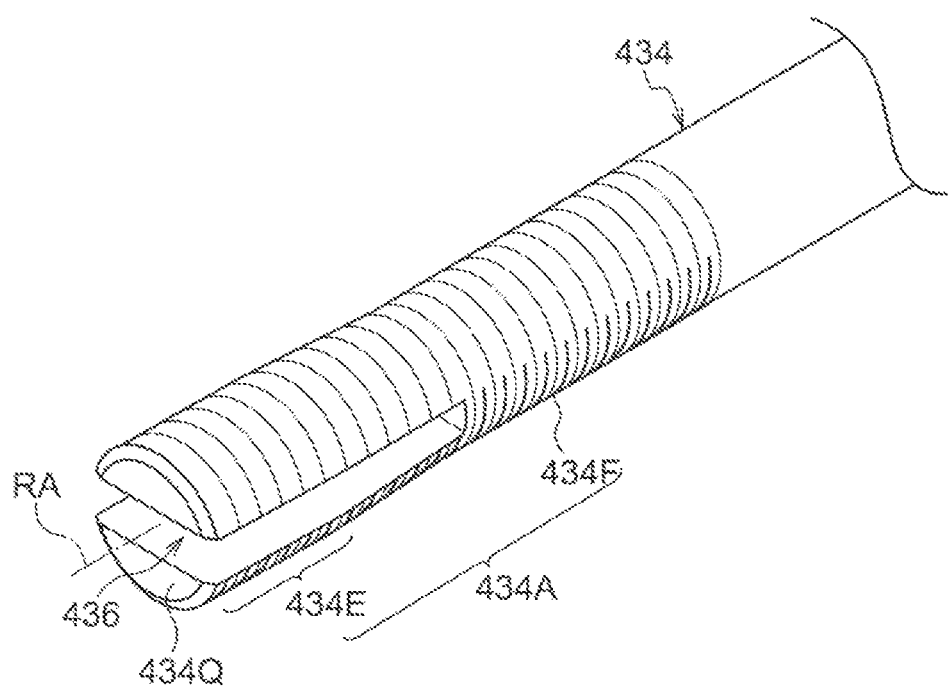
FIG. 7A is an enlarged perspective view showing the second-orientation end region of the rod of the dental coupling member according to Embodiment 4.
Figure 7B:
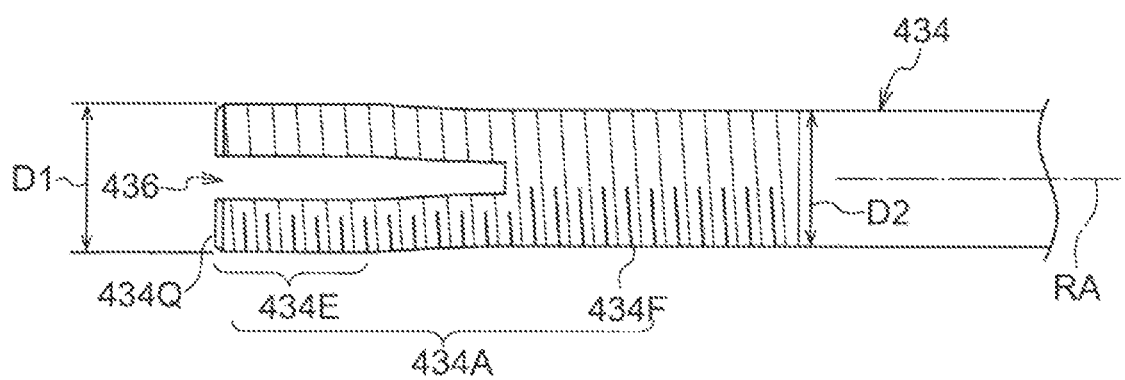
FIG. 7B is an enlarged side view showing the second-orientation end region of the rod of the dental coupling member according to Embodiment 4.

The dental coupling member according to Embodiment 4 has rod 434 shown in FIGS. 7A and 7B. This rod 434 has gap part 436 formed in second-orientation end region 434Q. Gap part 436 is a slit formed in a shape that has a width changing in the depth direction (the direction from the second-orientation end region side of male screw part 434 toward the first-orientation end region side) and is substantially rotationally symmetric at a position passing through the axial center RA of rod 434 and about the axial center RA.

Since in Embodiment 4 the large width portion of gap part 436 is formed over a greater length, increased diameter part 434E of rod 434, namely the portion with outer diameter D1, covers a certain range in the axial direction. In other words, in Embodiment 4, the range with outer diameter D1 is long in the axial direction of rod 434 compared to Embodiment 1.

Also in Embodiment 4, male screw part 434A includes increased diameter part 434E and constant diameter part 434F. Meanwhile, inner tube 32 also has a constant inner diameter in female screw part 32B in Embodiment 4. Accordingly, large torque is required when male screw part 434A is threaded into and rotated in female screw part 32B, compared to a rod having a male screw part with no formation of increased diameter part 434E. After the amount of screwing of male screw part 434A is adjusted, male screw part 434A is restrained from becoming loose relative to female screw part 32B.

In Embodiment 4, the range having the constant outer diameter D1 as the increased diameter part of rod 434 is long in the axial direction of rod 434. Thus, compared to Embodiments 1 through 3, large frictional force can be generated by allowing the increased diameter part to make contact with female screw part 32B over a wide range. Although second-orientation end region 434Q of male screw part 434A of rod 434 is segmented into two segment regions in FIGS. 7A and 7B, it may be segmented into three or more segment regions.

2-5. Embodiment 5

Figure 8A:
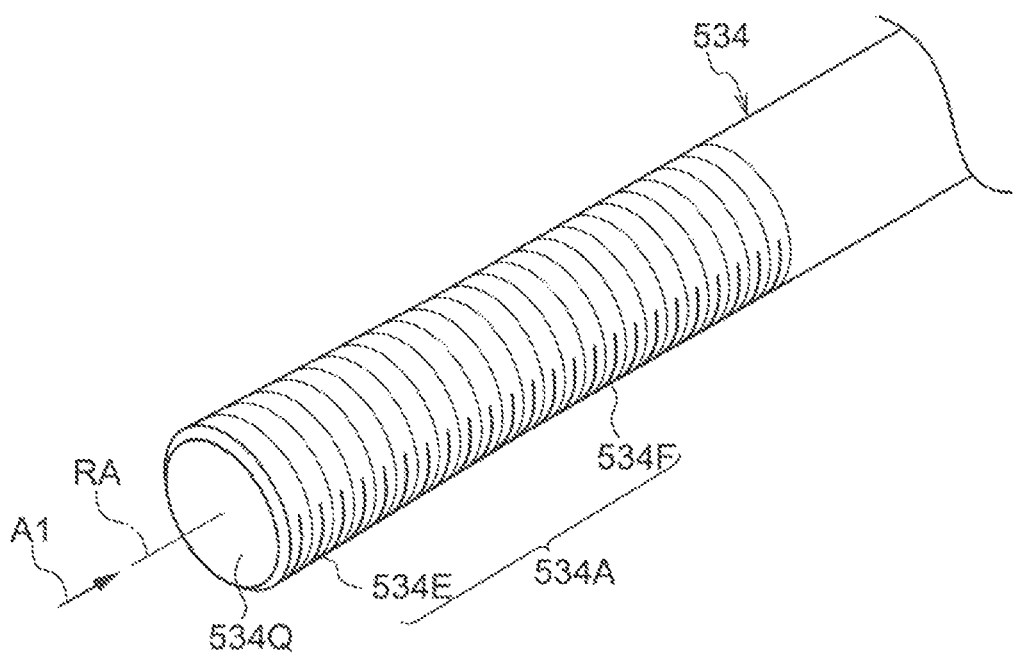
FIG. 8A is an enlarged perspective view showing the second-orientation end region of the rod of the dental coupling member according to Embodiment 5.
Figure 8B:
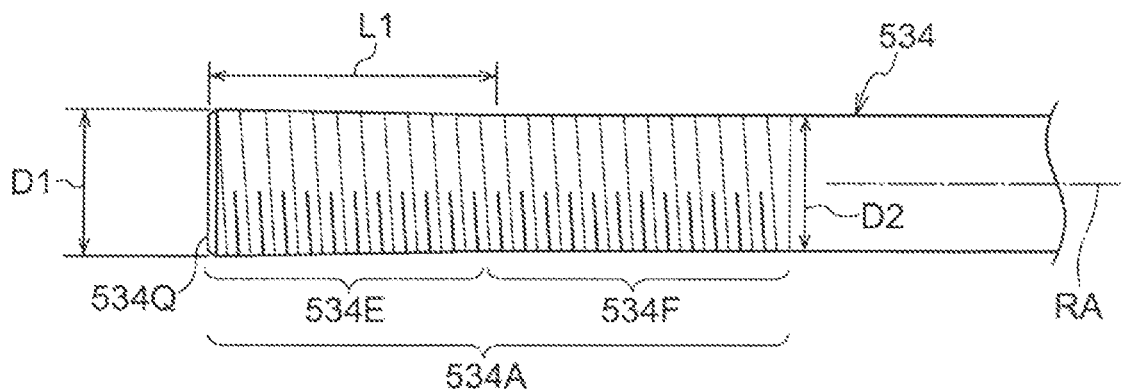
FIG. 8B is an enlarged side view showing the second-orientation end region of the rod of the dental coupling member according to Embodiment 5.

The dental coupling member according to Embodiment 5 has rod 534 shown in FIGS. 8A and 8B. As shown in FIGS. 8A and 8B, rod 534 has increased diameter part 534E of a truncated cone shape formed in a portion of male screw part 534A, in particular in a portion with a predetermined length L1 in second-orientation end region 534Q of male screw part 534A. Of male screw part 534A, the portion on first-orientation end region 34P (see FIGS. 3A and 3B) side (the right-hand portion in FIG. 8B) is a portion with no formation of increased diameter part 534E and is constant diameter part 534F with an outer diameter D2 smaller than that of increased diameter part 534E.

The outer diameter D2 of constant diameter part 534F is constant in the axial direction of rod 534. In contrast, the outer diameter D1 of increased diameter part 534E increases from the portion continuous with constant diameter part 534F toward second-orientation end region 534Q side. The outer diameter D1 of increased diameter part 534E is then at its maximum at the end on second-orientation end region 534Q side. Although outer diameter D1 linearly increases toward second-orientation end region 534Q side in the example shown in FIGS. 8A and 8B, the shape of increased diameter part 534E is not limited to such a shape with outer diameter D1 increasing linearly. However, a shape with outer diameter D1 increasing linearly does not cause a steep change in the outer diameter D1 of increased diameter part 534E; thus breakage of increased diameter part 534E due to local stress on increased diameter part 534E that occurs during screwing can be restrained.

To form increased diameter part 534E, at a preceding stage in which male screw part 534A is formed during the manufacture of rod 534, for example, the length L1 portion on second-orientation end region 534Q side is formed such that the outer diameter increases toward the end on second-orientation end region 534Q side. Then, by forming male screw part 534A in a predetermined range including the length L1 portion, male screw part 534A including increased diameter part 534E can be formed on rod 534.

Constant diameter part 534F and increased diameter part 534E are of circular shapes that are substantially rotationally symmetric relative to the axis RA and centered at the axis RA. The outer diameter D2 of constant diameter part 534F is sized to be screwed with female screw part 32B. Further, the outer diameter D1 of increased diameter part 534E is sized to be screwed with female screw part 32B even in the portion with the largest outer diameter. The radial clearance between male screw part 534A and female screw part 32B is constant between constant diameter part 534F and female screw part 32B but gradually becomes narrower between increased diameter part 534E and female screw part 32B toward second-orientation end region 534Q side. When male screw part 534A and female screw part 32B are in contact with each other, this clearance is zero. In reality, however, a slight clearance forms between the flank of male screw part 534A and the flank of female screw part 32B, and the clearance between large diameter part 534E and female screw part 32B is narrower than the clearance between constant diameter part 534F and female screw part 32B. Increased diameter part 534E creates portions with different radial clearances between the male screw part and the female screw part in male screw part 32A. Increased diameter part 534E and constant diameter part 534F are examples of "different-torque part" and of "different-diameter part".

When male screw part 534A is screwed with female screw part 32B, male screw part 534A makes stronger contact with female screw part 32B and generates larger frictional force against female screw part 32B during rotation in increased diameter part 534E than in constant diameter part 534F. That is, large torque is required for rotation during screwing with female screw part 32B compared to a male screw part of a structure without increased diameter part 534E.

Inner tube 32 has a constant inner diameter in female screw part 32B. In other words, there is no portion where the inner diameter of the inner peripheral surface of inner tube 32 changes. Thus, inner tube 32 is of a shape that facilitates the formation of female screw part 32B.

Figure 8C:
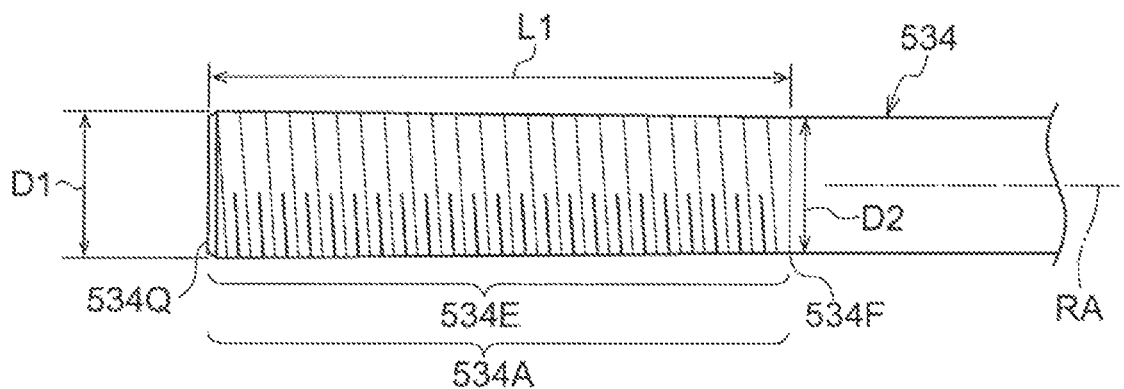
FIG. 8C is an enlarged side view showing the second-orientation end region of another rod of the dental coupling member according to Embodiment 5.

Rod 534 according to the variation shown in FIG. 8C may be used in Embodiment 5. With rod 534 as the variation, the outer diameter D1 of male screw part 534A gradually increases toward the end on second-orientation end region 534Q side substantially over the entire range in which male screw part 534A is formed. In other words, screwing large-diameter part 534E, an example of the different-diameter part, is formed substantially throughout male screw part 534A.

In such a structure with outer diameter D1 changing substantially throughout male screw part 534A, the clearance between male screw part 534A and female screw part 32B (an example of the screwed part) continuously changes substantially throughout male screw part 534A. This structure also produces a structure that gives at least two distinct lengths of radial clearance between the screwing part and the screwed part.

2-6. Embodiment 6

Figure 9:
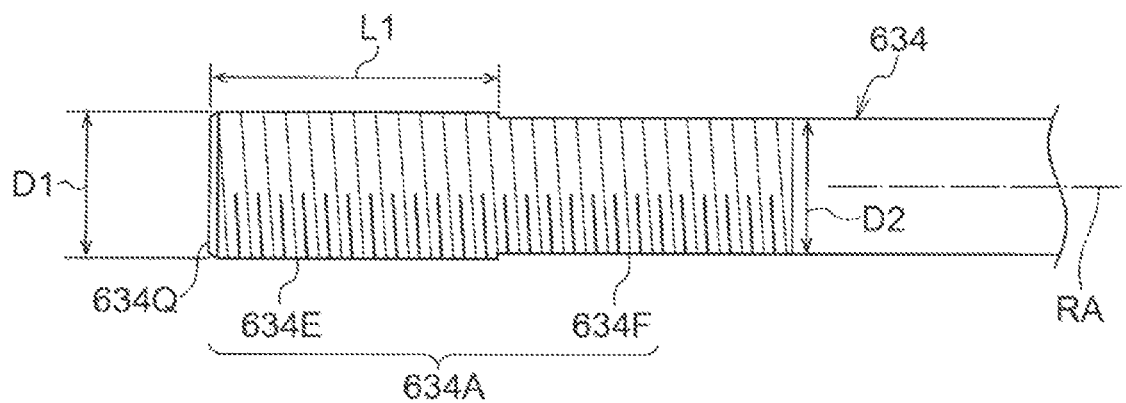
FIG. 9 is an enlarged side view showing the second-orientation end region of the rod of the dental coupling member according to Embodiment 6.

The dental coupling member according to Embodiment 6 has rod 634 shown in FIG. 9. This rod 634 has increased diameter part 634E of a cylindrical shape, formed in second-orientation end region 634Q of male screw part 634A. This increased diameter part 634E is of a shape that has a constant outer diameter D1 over the range of a certain length L1 from the end on second-orientation end region 634Q side. Increased diameter part 634E and constant diameter part 634F are examples of "different-torque part" and of "different-diameter part".

Also in Embodiment 6, male screw part 634A includes increased diameter part 634E and constant diameter part 634F. In Embodiment 6, accordingly, large torque is required when male screw part 634A is threaded into and rotated in female screw part 32B, compared to a rod having a male screw part with no formation of increased diameter part 634E. After the amount of screwing of male screw part 634A is adjusted, male screw part 634A is restrained from becoming loose relative to female screw part 32B.

In Embodiment 6, increased diameter part 634E has the constant outer diameter D1 and spans a certain length L1 in the axial direction. Since the portion that makes strong contact with female screw part 32B spreads in the axial direction in male screw part 634A, namely the screwing part, a portion that generates large frictional force when screwing male screw part 634A and female screw part 32B together can be secured to be wide, stabilizing the torque required for rotation when male screw part 634A is screwed with female screw part 32B.

2-7. Embodiment 7

Figure 10:
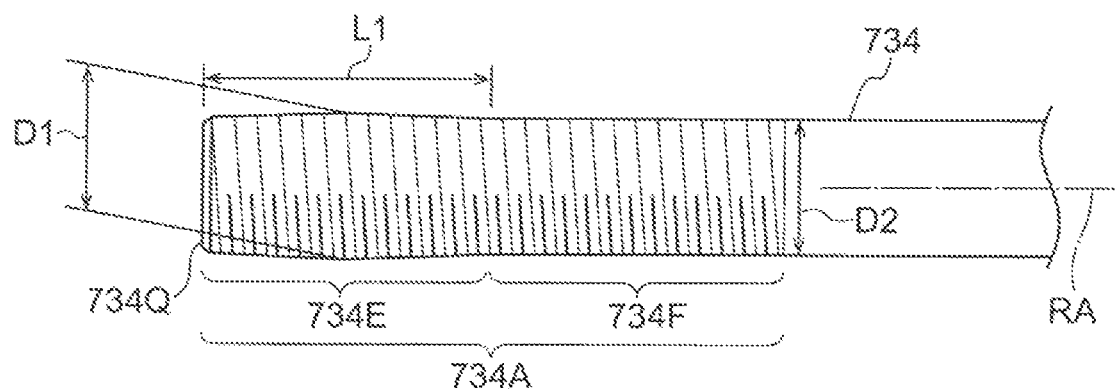
FIG. 10 is an enlarged side view showing the second-orientation end region of the rod of the dental coupling member according to Embodiment 7.

The dental coupling member according to Embodiment 7 has rod 734 shown in FIG. 10. This rod 734 has increased diameter part 734E of a barrel shape formed in second-orientation end region 734Q of male screw part 734A. Increased diameter part 734E is formed in the range of a certain length L1 from the end on the second-orientation end region 734Q side. In Embodiment 7, increased diameter part 734E is shaped such that outer diameter D1 is at its maximum at the center of this range of length L1 and outer diameter D1 decreases as it goes away from the center. Increased diameter part 734E and constant diameter part 734F are examples of "different-torque part" and of "different-diameter part".

In Embodiment 7, male screw part 734A includes increased diameter part 734E and constant diameter part 734F. In Embodiment 7, accordingly, large torque is required when male screw part 734A is threaded into and rotated in female screw part 32B, compared to a rod having a male screw part with no formation of increased diameter part 734E. After the amount of screwing of male screw part 734A is adjusted, male screw part 734A is restrained from becoming loose relative to female screw part 32B.

In Embodiment 7, increased diameter part 734E is shaped such that it tapers from the center of increased diameter part 734E in the axial direction toward the end on second-orientation end region 734Q side. Accordingly, male screw part 734A is easy to screw with female screw part 32B in an early stage of screwing male screw part 734A with female screw part 32B.

2-8. Embodiment 8

Figure 11A:
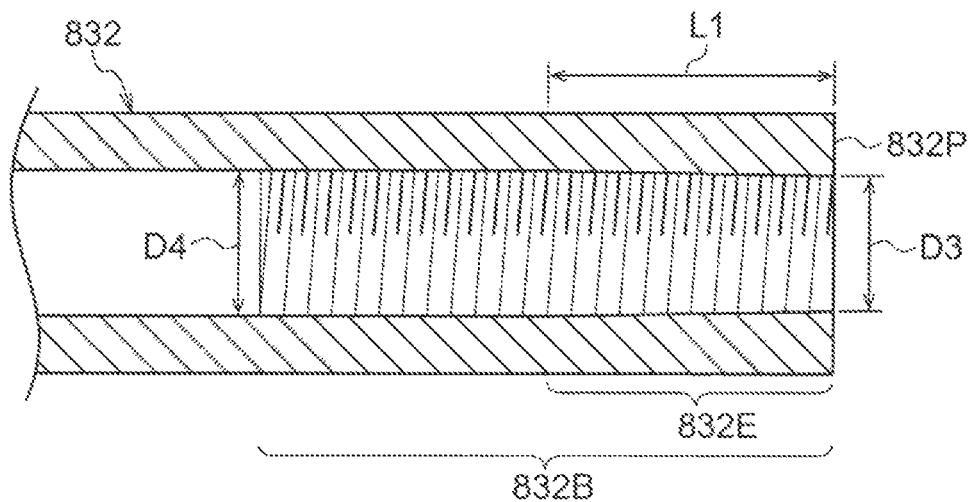
FIG. 11A is an enlarged cross-sectional view showing the second-orientation end region of an inner tube of the dental coupling member according to Embodiment 8.

The dental coupling member according to Embodiment 8 has inner tube 832 shown in FIG. 11A. This inner tube 832 has inner-diameter reduced part 832E formed in female screw part 832B such that female screw part 832B is a different-diameter part. In the example shown in FIG. 11A, female screw part 832B has inner-diameter reduced part 832E with an inner diameter D3 that decreases from the center in the axial direction toward the end on first-orientation end region 832P side. In contrast, female screw part 832B has a constant inner diameter D4 in the portion where inner-diameter reduced part 832E is not formed. The male screw part in Embodiment 8 has a constant outer diameter in the axial direction of the rod.

In Embodiment 8, such a portion with decreasing inner diameter D3 within female screw part 832B is inner-diameter reduced part 832E. The clearance between female screw part 832B and the male screw part of the rod is constant in the portion where inner-diameter reduced part 832E is not formed, but it gradually becomes narrower toward the end on first-orientation end region 832P side of inner tube 832 in the portion where inner-diameter reduced part 832E is formed.

Accordingly, also in Embodiment 8, large torque is required when male screw part 34A is threaded into and rotated in female screw part 832B, compared to an inner tube having a female screw part with no formation of the different-diameter part. Thus, after the amount of screwing of the male screw part is adjusted, the male screw part is restrained from becoming loose relative to female screw part 832B. Although inner-diameter reduced part 832E is formed as a part of female screw part 832B in FIG. 11A, the entire portion of female screw part 832B may be inner-diameter reduced part 832E. Additionally, although in FIG. 11A female screw part 832B is shaped such that its inner diameter decreases from the center in the axial direction toward the end on first-orientation end region 832P side, it may have a barrel shape with inner diameter D3 being at its maximum in the center of the range of length L1 and decreasing as it goes away from the center.

Figure 11B:
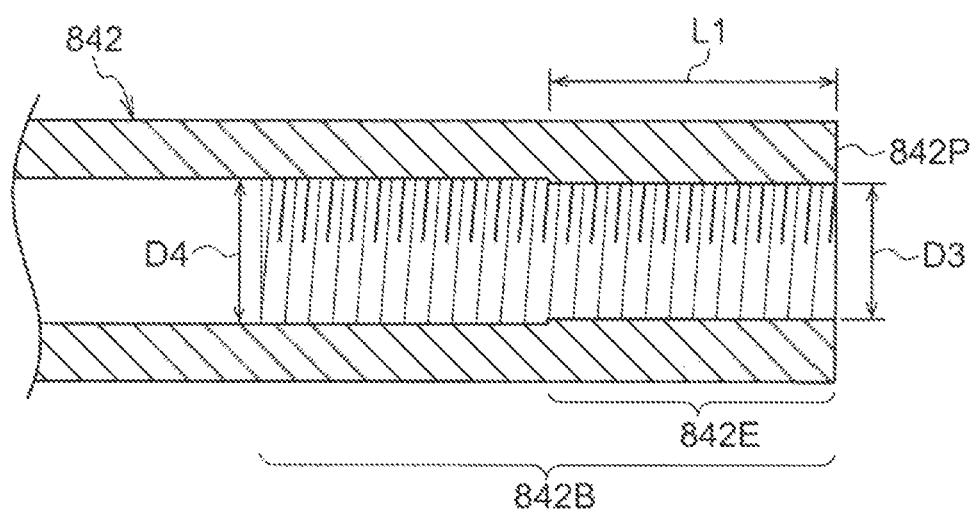
FIG. 11B is an enlarged cross-sectional view showing the second-orientation end region of another inner tube of the dental coupling member according to Embodiment 8.

Inner tube 842 according to a second variation shown in FIG. 11B may be used in Embodiment 8. With inner tube 842 as the second variation, inner-diameter reduced part 842E is of a shape having a constant inner diameter D3 over the range of a certain length L1 from the end on first-orientation end region 842P side. In the second variation, inner-diameter reduced part 842E spans a certain length L1 in the axial direction. Since the portion that makes strong contact with the male screw part spreads in the axial direction in female screw part 842B, the torque required for rotation when the male screw part is screwed with female screw part 842B is stabilized.

2-9. Embodiment 9

Figure 12A:
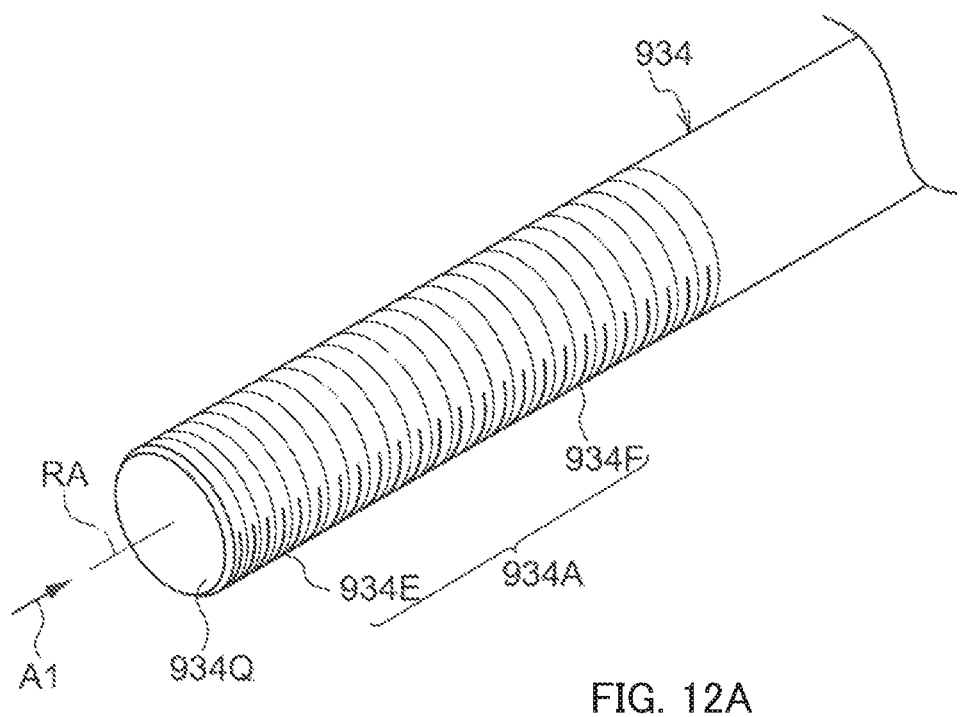
FIG. 12A is an enlarged perspective view showing the second-orientation end region of the rod of the dental coupling member according to Embodiment 9.
Figure 12B:
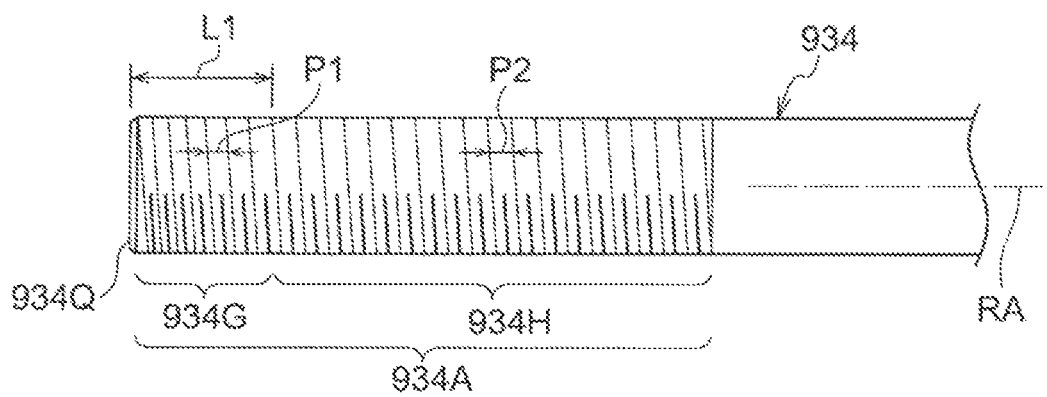
FIG. 12B is an enlarged side view showing the second-orientation end region of the rod of the dental coupling member according to Embodiment 9.

The dental coupling member according to Embodiment 9 has rod 934 shown in FIGS. 12A and 12B. As shown in FIGS. 12A and 12B, rod 934 has screwing small-pitch part 934G formed in the portion where male screw part 934A is formed, in particular a portion with a predetermined length L1 in second-orientation end region 934Q. Of male screw part 934A, a portion on first-orientation end region 34P (see FIGS. 3A and 3B) side (the right-hand portion in FIG. 12B) is a portion with no formation of screwing small-pitch part 934G and is screwing large-pitch part 934H having pitch P2 greater than the pitch of screwing small-pitch part 934G.

The pitch P2 of screwing large-pitch part 934H is constant in the axial direction of rod 934 and is equal to the pitch of female screw part 32B. In contrast, the pitch P1 of screwing small-pitch part 934G decreases from the portion continuous with screwing large-pitch part 934H toward the end on second-orientation end region 934Q side. The pitch P1 of screwing small-pitch part 934G is then at its minimum at the end on second-orientation end region 934Q side. Although pitch P1 linearly decreases toward the end on second-orientation end region 934Q side in the example shown in FIGS. 12A and 12B, the shape of screwing small-pitch part 934G is not limited to such a shape with pitch P1 decreasing linearly. However, a shape with pitch P1 decreasing linearly does not cause a steep change in the pitch P1 of screwing small-pitch part 934G; thus breakage of screwing small-pitch part 934G due to local stress on screwing small-pitch part 934G that occurs during screwing can be restrained.

To form screwing small-pitch part 934G, a male screw with pitch P1 is formed in a predetermined range including the length L1 portion, for example, at a stage of forming male screw part 934A during the manufacture of rod 934. Then, by forming a male screw with pitch P2 in the range of male screw part 934A excluding the predetermined range, male screw part 934A including screwing small-pitch part 934G can be formed on rod 934.

Screwing large-pitch part 934H and screwing small-pitch part 934G are substantially symmetric in the circumferential direction, that is, are circular shapes centered at axis RA when seen in the direction of axis RA (in the direction of arrow A1). The pitch P2 of screwing large-pitch part 934H is sized to be screwed with female screw part 32B. Further, the pitch P1 of screwing small-pitch part 934G is sized to be screwed with female screw part 32B even in the portion with the smallest pitch. The pitch difference between male screw part 934A and female screw part 32B is constant between screwing large-pitch part 934H and female screw part 32B (is virtually zero, for example), but gradually increases between screwing small-pitch part 934G and female screw part 32B toward the end on second-orientation end region 934Q side. Screwing large-pitch part 934H and screwing small-pitch part 934G are examples of "different-torque part" and of "different-pitch part".

When male screw part 934A is screwed with female screw part 32B, male screw part 934A makes stronger contact with female screw part 32B and generates larger frictional force against female screw part 32B during rotation in screwing small-pitch part 934G than in screwing large-pitch part 934H. That is, large torque is required for rotation during screwing with female screw part 32B compared to a male screw part of a structure without screwing small-pitch part 934G.

Inner tube 32 has a constant inner diameter in female screw part 32B. In other words, there is no portion where the inner diameter of the inner peripheral surface of inner tube 32 changes. Thus, inner tube 32 is of a shape that facilitates the formation of female screw part 32B.

Figure 12C:
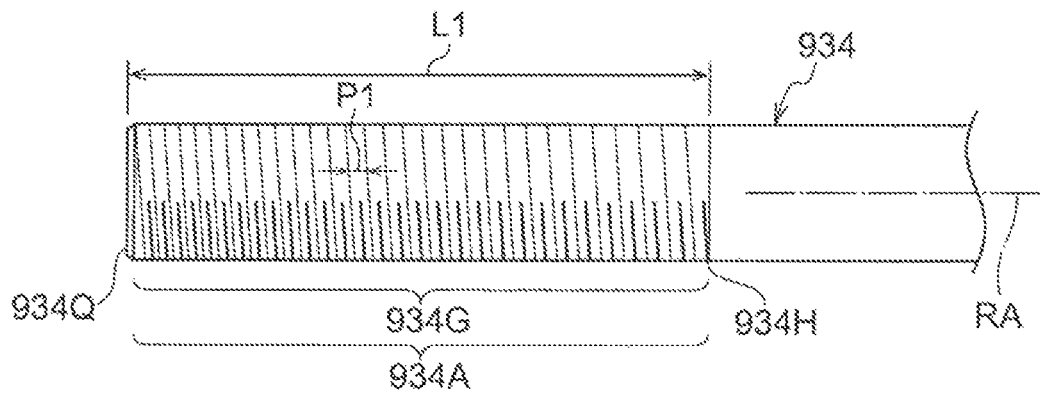
FIG. 12C is an enlarged side view showing the second-orientation end region of another rod of the dental coupling member according to Embodiment 9.

Rod 934 according to the variation shown in FIG. 12C may be used in Embodiment 9. In rod 934 as the variation, the pitch P1 of male screw part 934A gradually degreases toward the end on second-orientation end region 934Q side substantially in the entire range in which male screw part 934A is formed. In other words, screwing small-pitch part 934G, an example of the different-pitch part, is formed substantially throughout male screw part 934A.

With such a structure with pitch P1 changing substantially throughout male screw part 934A, the pitch difference between male screw part 934A and female screw part 32B (an example of the screwed part) continuously changes substantially throughout male screw part 934A. This structure also produces a structure that gives at least two distinct pitch differences between the screwing part and the screwed part.

2-10. Embodiment 10

Figure 13:
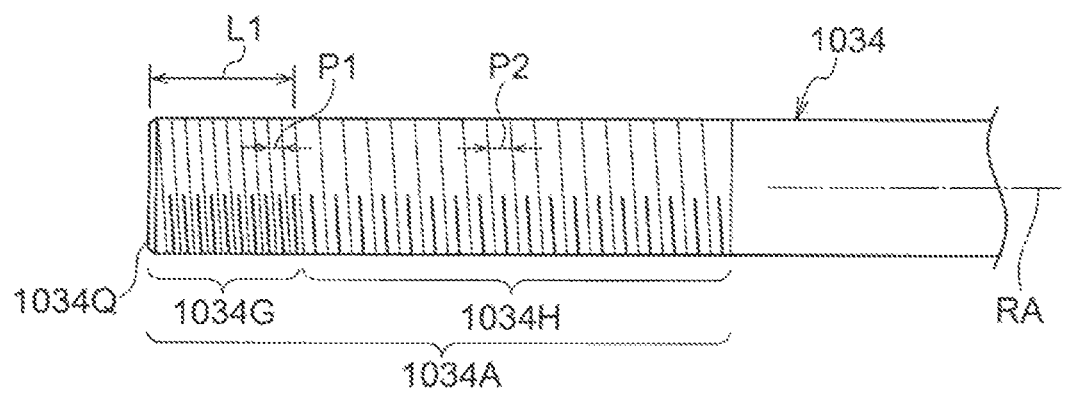
FIG. 13 is an enlarged side view showing the second-orientation end region of another rod of the dental coupling member according to Embodiment 10.

The dental coupling member according to Embodiment 10 has rod 1034 shown in FIG. 13. This rod 1034 has screwing small-pitch part 1034G formed in second-orientation end region 1034Q of male screw part 1034A. This screwing small-pitch part 1034G is of a shape having a constant pitch P1 over the range of a certain length L1 from the end on second-orientation end region 1034Q side.

In Embodiment 10, male screw part 1034A includes screwing small-pitch part 1034G and screwing large-pitch part 1034H. In Embodiment 10, accordingly, large torque is required when male screw part 1034A is threaded into and rotated in female screw part 32B, compared to a rod having a male screw part with no formation of screwing small-pitch part 1034G After the amount of screwing of male screw part 1034A is adjusted, male screw part 1034A is restrained from becoming loose relative to female screw part 32B.

In Embodiment 10, screwing small-pitch part 1034G has a constant pitch P1 and spans a certain length L1 in the axial direction. Since the portion that makes strong contact with female screw part spreads in the axial direction in male screw part 1034A, namely the screwing part, the torque required for rotation when male screw part 1034A is screwed with female screw part is stabilized.

2-11. Embodiment 11

Figure 14:
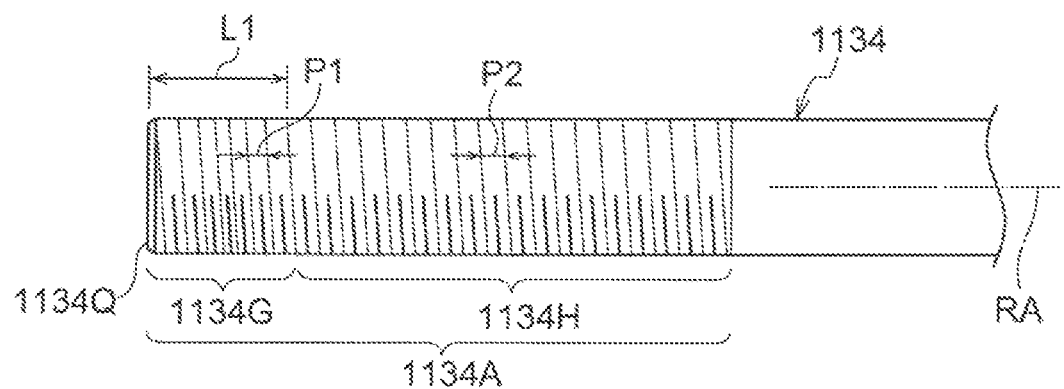
FIG. 14 is an enlarged side view showing the second-orientation end region of the rod of the dental coupling member according to Embodiment 11.

The dental coupling member according to Embodiment 11 has rod 1134 shown in FIG. 14. This rod 1134 has screwing small-pitch part 1134G formed in second-orientation end region 1134Q of male screw part 1134A. Screwing small-pitch part 1134G is formed in the range of a certain length L1 from the end on second-orientation end region 1134Q side. In Embodiment 11, rod 1134 is shaped such that pitch P1 is at its minimum at the center of this range of length L1 and pitch P1 increases as it goes away from the center.

Also in Embodiment 11, male screw part 1134A includes screwing small-pitch part 1134G and screwing large-pitch part 1134H. In Embodiment 11, accordingly, large torque is required when male screw part 1134A is threaded into and rotated in female screw part 32B, compared to a rod having a male screw part with no formation of screwing small-pitch part 1134G After the amount of screwing of male screw part 1134A is adjusted, male screw part 1134A is restrained from becoming loose relative to female screw part 32B.

In Embodiment 11, rod 1134 is shaped such that the pitch increases from the center of screwing small-pitch part 1134G in the axial direction toward the end on the second-orientation end region 1134Q side. In other words, at the end on the second-orientation end region 1134Q side, the pitch of male screw part 1134A is close to the pitch of female screw part. Accordingly, male screw part 1134A is easy to screw with female screw part 32B in an early stage of screwing male screw part 1134A with female screw part 32B.

2-12. Embodiment 12

Figure 15A:
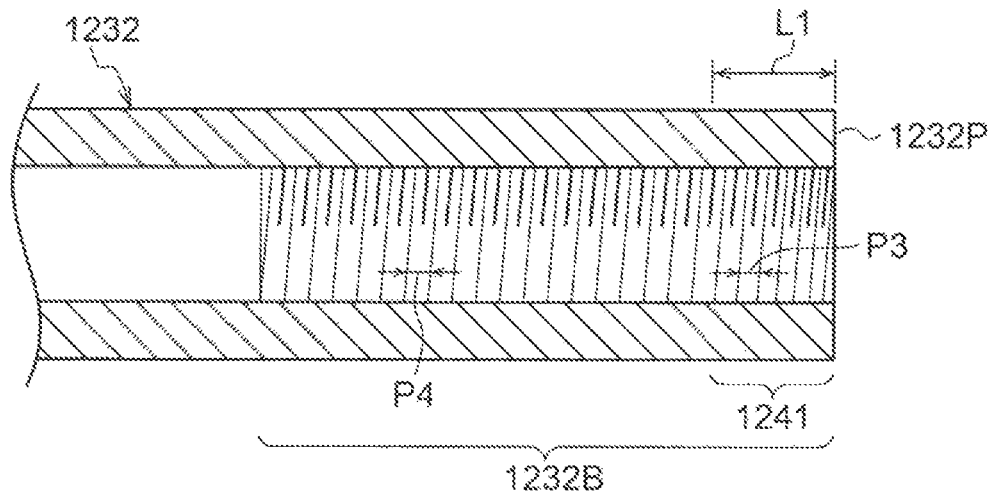
FIG. 15A is an enlarged cross-sectional view showing the second-orientation end region of an inner tube of the dental coupling member according to Embodiment 12.

The dental coupling member according to Embodiment 12 has inner tube 1232 shown in FIG. 15A. This inner tube 1232 has a different-pitch part formed in female screw part 1232B. In the example shown in FIG. 15A, pitch-reduced part 1232G is formed in the range of a certain length L1 from the end on first-orientation end region 1232P side, with pitch P3 decreasing from the center of female screw part 1232B in the axial direction toward the end on first-orientation end region 1232P side. In contrast, female screw part 1232B has a constant pitch P4 in the portion where pitch-reduced part 1232G is not formed. The male screw part in Embodiment 12 has a constant pitch in the axial direction of the rod.

In Embodiment 12, such a portion of female screw part 1232B where pitch P3 decreases is pitch-reduced part 1232G The pitch difference between female screw part 1232B and the male screw part of the rod is constant in the portion where pitch-reduced part 1232G is not formed, but it gradually increases toward the end on first-orientation end region 1232P side of inner tube 1232 in the portion where pitch-reduced part 1232G is formed.

Accordingly, also in Embodiment 12, large torque is required when male screw part 34A is threaded into and rotated in female screw part 1232B, compared to an inner tube having a female screw part with no formation of the pitch-reduced part. Thus, after the amount of screwing of the male screw part is adjusted, the male screw part is restrained from becoming loose relative to female screw part 1232B. In FIG. 15A, female screw part 1232B is shaped such that the pitch decreases from the center in the axial direction toward the end on first-orientation end region 1232P side. However, it may have a shape with the pitch increasing from the center in the axial direction toward the end on first-orientation end region 1232P side, or a barrel shape with the pitch being at its maximum in the center of the range of length L1 and the inner diameter decreasing as it goes away from the center.

Figure 15B:
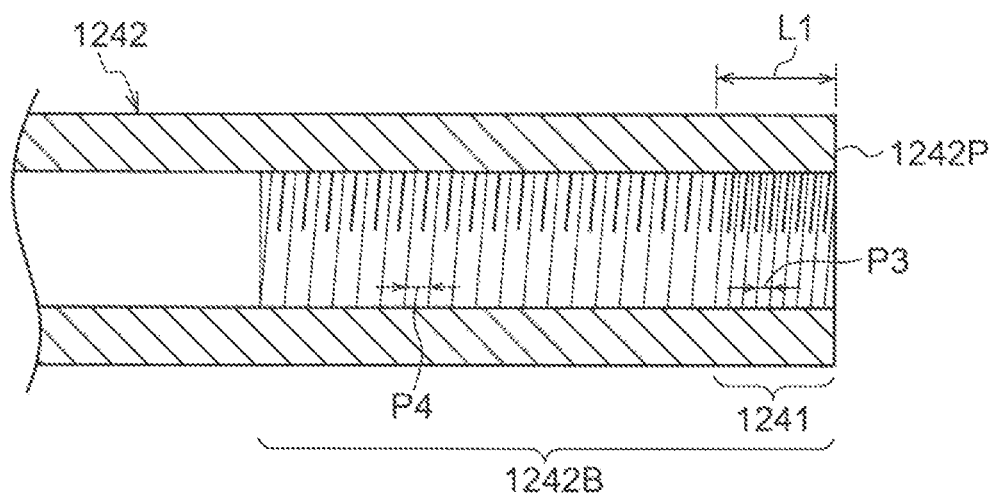
FIG. 15B is an enlarged cross-sectional view showing the second-orientation end region of another inner tube of the dental coupling member according to Embodiment 12.

Inner tube 1242 according to a second variation shown in FIG. 15B may be used in Embodiment 12. Inner tube 1242 in the second variation is shaped such that pitch-reduced part 1232G has a constant pitch P3 over the range of a certain length L1 from the end on first-orientation end region 1242P side. In the second variation, pitch-reduced part 1232G spans a certain length L1 in the axial direction. Since the portion that makes strong contact with the male screw part spreads in the axial direction in female screw part 1242B, the torque required for rotation when the male screw part is screwed with female screw part 42B is stabilized.

2-13. Embodiment 13

Figure 16:
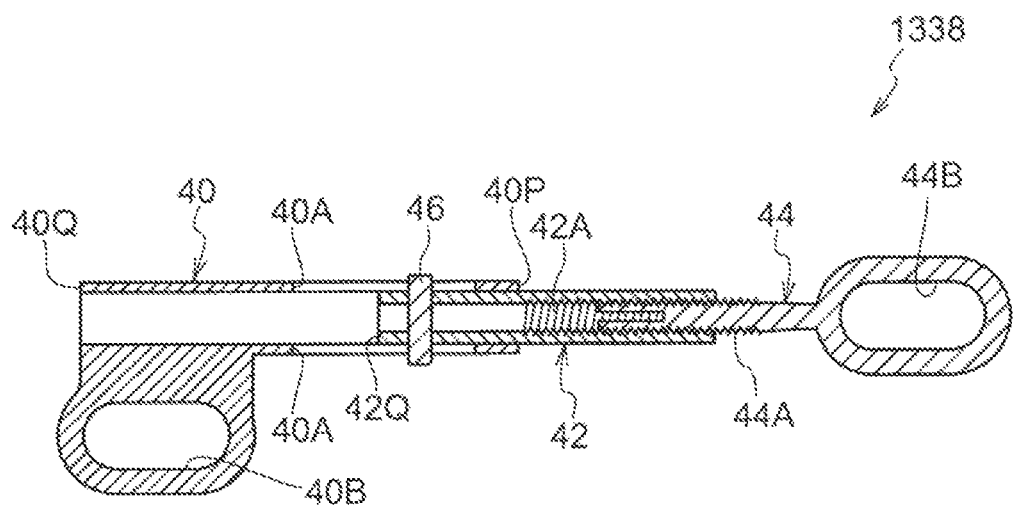
FIG. 16 is a cross-sectional view showing the dental coupling member according to Embodiment 13.

Next, using FIG. 16, dental coupling member 1338 for a mouthpiece according to Embodiment 13 of the present invention is described.

Dental coupling member 1338 according to Embodiment 13 has tubular outer tube 40 being open both at the end on first-orientation end region 40P side and at the end on second-orientation end region 40Q side in the axial direction, tubular inner tube 42 slidably provided in outer tube 40, and rod 44 to be engaged with inner tube 42.

Outer tube 40 has a pair of slits 40A formed at positions opposing each other along the axial direction of outer tube 40, between the end on first-orientation end region 40P side and the end on second-orientation end region 40Q side. In the vicinity of second-orientation end region 42Q of inner tube 42, columnar pin 46 has been attached so as to penetrate inner tube 42 in the radial direction. Slit 40A is an example of "limiting part".

The longer diameter of pin 46 is sized to be slightly smaller than the width of slit 40A in outer tube 40. The opposite ends of pin 46 in the longer diameter direction project from the outer peripheral surface of inner tube 42, and are slidably inserted in the pair of slits 40A, respectively.

Dental coupling member 1338 is adjustable in length by sliding of inner tube 42 in outer tube 40. In doing so, the sliding of inner tube 42 in both axial directions is limited by abutment of pin 46 attached on inner tube 42 against the opposite ends of slits 40A in outer tube 40 (the right and left ends in FIG. 16).

Embodiment 13 limits the sliding of inner tube 42 in outer tube 40 in both axial directions by making pin 46 attached on inner tube 42 abut against the opposite ends of slits 40A formed in outer tube 40. This can make dental coupling member 1338 compact in size compared to a configuration providing an inner tube like a nut outside of outer tube 40 or a configuration that makes inner tube 42 and/or rod 44 abut against an outer end of outer tube 40.

Additionally, since the opposite ends of pin 46 are inserted in pair of slits 40A formed in outer peripheral surface of outer tube 40, respectively, inner tube 42 can be further restrained from rotating about the axis relative to outer tube 40 when inner tube 42 slides in outer tube 40.

Also in Embodiment 13, male screw part 44A includes an increased diameter part and a constant diameter part (see FIGS. 4A, 4B, 5, 6, 7A, 7B, 8A, 8B, 8C, 9, 10, 11A, and 11B) or a screwing small-pitch part and a screwing large-pitch part (FIGS. 12A, 12B, 13, and 14). Thus, large torque is required when male screw part 44A is threaded into and rotated in the female screw part, and male screw part 44A is restrained from becoming loose relative to the female screw part.

2-14. Embodiment 14

Figure 17:
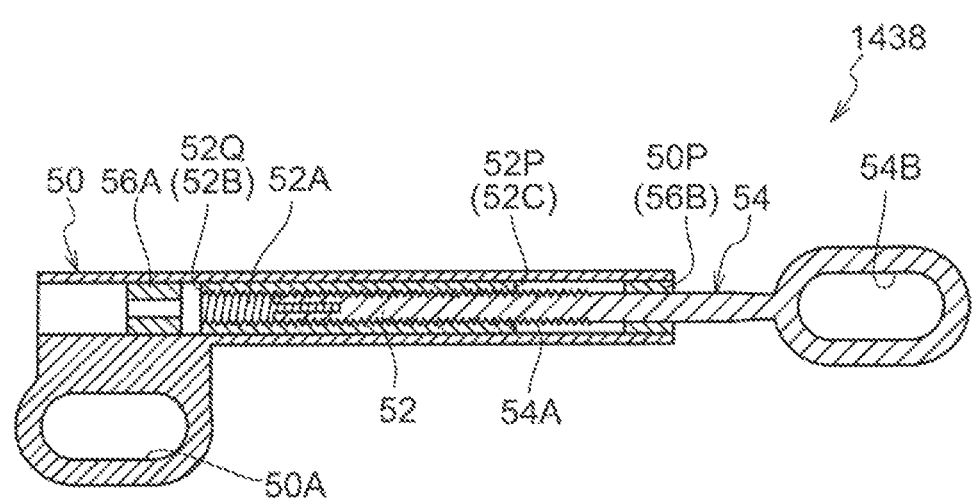
FIG. 17 is a cross-sectional view showing the dental coupling member according to Embodiment 14.

Next, using FIG. 17, dental coupling member 1438 for a mouthpiece according to Embodiment 14 of the present invention is described.

Dental coupling member 1438 has tubular outer tube 50 being open both at the end on first-orientation end region 50P side and at the end on second-orientation end region side, tubular inner tube 52 slidably provided in outer tube 50, and rod 54 to be engaged with inner tube 52.

Within outer tube 50, a pair of stoppers 56A, 56B are provided between the end on first-orientation end region 50P side and the end on second-orientation end region side. Stopper 56A, 56B are of a cylindrical shape with a hollow part and are fixed on the inner peripheral surface of outer tube 50. Stoppers 56A and 56B are examples of "limiting part".

The length of inner tube 52 in the axial direction is shorter than the length between stoppers 56A and 56B, namely the length from the lower end of stopper 56A on the upper end side (the side of the left end in FIG. 17) to the upper end of stopper 56B on the lower end side (the side of the right end in FIG. 17), with inner tube 52 inserted between stoppers 56A and 56B in outer tube 50.

Second-orientation end region 52P of inner tube 52 is abutting part 52B to abut against the lower end of stopper 56A, while first-orientation end region 52P of inner tube 52 is abutting part 52C to abut against the upper end of stopper 56B.

On rod 54, lower eyelet 54B in the first-orientation end region is exposed from outer tube 50, with male screw part 54A in the second-orientation end region being inserted in outer tube 50 through the hollow part of stopper 56B and screwed with female screw part 52A of inner tube 52.

Dental coupling member 1438 is adjustable in length by sliding of inner tube 52 between stoppers 56A and 56B in outer tube 50. In doing so, the sliding of inner tube 52 in both axial directions is limited by abutment of abutting parts 52B, 52C of inner tube 52 against stoppers 56A, 56B, respectively.

Embodiment 14 limits the sliding of inner tube 52 within outer tube 50 in both axial directions by means of stopper 56A, 56B provided in outer tube 50 between the end on first-orientation end region 50P side and the end on second-orientation end region side. This can make dental coupling member 1438 compact in size compared to a configuration providing an inner tube or stoppers outside of outer tube 50.

Also in Embodiment 14, male screw part 54A includes an increased diameter part and a constant diameter part (see FIGS. 4A, 4B, 5, 6, 7A, 7B, 8A, 8B, 8C, 9, 10, 11A, and 11B), or a screwing small-pitch part and a screwing large-pitch part (FIGS. 12A, 12B, 13, and 14). Thus, large torque is required when male screw part 54A is threaded into and rotated in the female screw part, and male screw part 54A is restrained from becoming loose relative to the female screw part.

2-15. Embodiment 15

Figure 18:
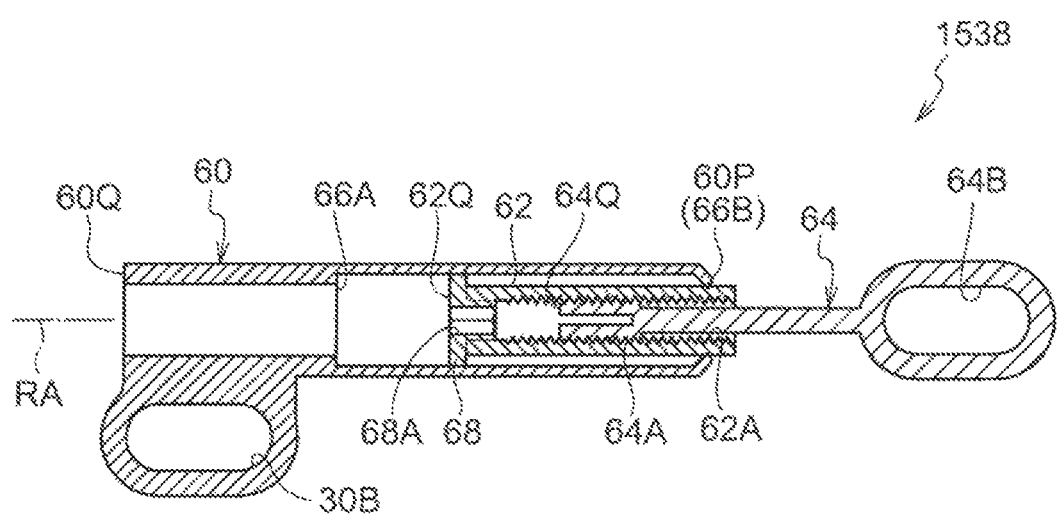
FIG. 18 is a cross-sectional view showing the dental coupling member according to Embodiment 15.

Next, using FIG. 18, dental coupling member 1538 for a mouthpiece according to Embodiment 15 of the present invention is described.

Dental coupling member 1538 has tubular outer tube 60 being open at the end on first-orientation end region 60P side and at the end on second-orientation end region 60Q side, tubular inner tube 62 slidably provided in outer tube 60, and rod 64 to be engaged with inner tube 62.

Within outer tube 60, decreased diameter parts 66A, 66B with a smaller inner diameter than the inner diameter of the other portion of outer tube 60 are formed between the end on first-orientation end region 60P side and the end on second-orientation end region 60Q side. Decreased diameter part 66A in second-orientation end region 60Q of outer tube 60 is formed by increasing the thickness of outer tube 60, whereas decreased diameter part 66B in first-orientation end region 60P of outer tube 60 is formed by crimping the lower end of outer tube 60. Decreased diameter parts 66A and 66B are examples of "limiting part".

In second-orientation end region 62Q of inner tube 62, increased diameter part 68 with a larger outer diameter than the outer diameter of the other portion of inner tube 62 is integrally formed, and increased diameter part 68 of inner tube 62 can slide between decreased diameter parts 66A and 66B of outer tube 60.

Insertion groove 68A is formed in the center of the end surface of increased diameter part 68 in second-orientation end region 62Q of inner tube 62. Insertion groove 68A is hexagonal, allowing insertion of a tool such as a hexagonal wrench.

On Rod 64, male screw part 64A formed in second-orientation end region 64Q has been screwed with female screw part 62A formed on the inner peripheral surface of inner tube 62.

Dental coupling member 1538 is adjustable in length by sliding of inner tube 62 in outer tube 60. In doing so, the sliding of inner tube 62 in both axial directions is limited by abutment of increased diameter part 68 of inner tube 62 against decreased diameter part 66A or decreased diameter part 66B of outer tube 60.

To adjust the position of rod 64 relative to inner tube 62, a hexagonal wrench is inserted into insertion groove 68A of increased diameter part 68 of inner tube 62 from the open end of outer tube 60 on second-orientation end region 60Q side. Then, the hexagonal wrench is rotated about the axis to rotate inner tube 62 about the axis, thereby adjusting the amount of screwing of male screw part 64A of rod 64 into female screw part 62A of inner tube 62.

Embodiment 15 limits the sliding of inner tube 62 within outer tube 60 in both axial directions by means of decreased diameter parts 66A, 66B formed in outer tube 60 between the end on first-orientation end region 60P side and the end on second-orientation end region 60Q side.

This can make dental coupling member 1538 compact in size compared to a configuration providing a member like a nut outside of outer tube 60 or a configuration that brings inner tube 62 and/or rod 64 into contact with an outer end of outer tube 60.

Embodiment 15 also allows the axial position of rod 64 relative to inner tube 62 to be adjusted by rotating inner tube 62 about the axis center RA, without rotation of rod 64 about the axis. Thus, the length of dental coupling member 1538 can be easily adjusted with lower eyelet 64B of rod 64 remaining engaged with flange 26 in FIG. 1.

Also in Embodiment 15, male screw part 64A includes an increased diameter part and a constant diameter part (see FIGS. 4A, 4B, 5, 6, 7A, 7B, 8A, 8B, 8C, 9, 10, 11A, and 11B), or a screwing small-pitch part and a screwing large-pitch part (FIGS. 12A, 12B, 13, and 14). Thus, large torque is required when male screw part 64A is threaded into and rotated in female screw part, and male screw part 64A is restrained from becoming loose relative to the female screw part.

2-16. Embodiment 16

Figure 19:
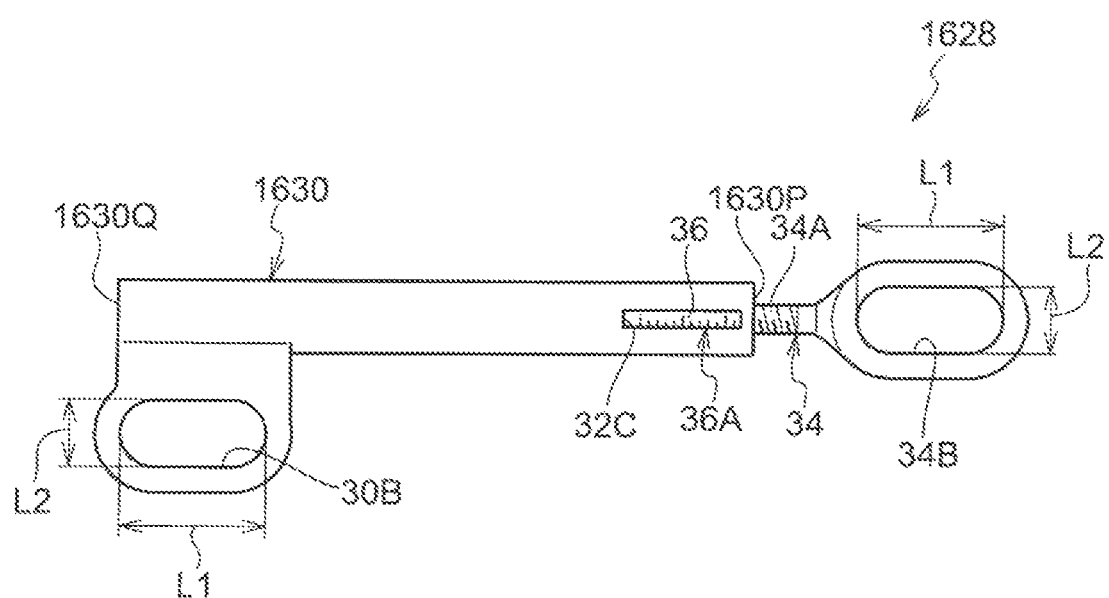
FIG. 19 is a plan view showing the dental coupling member according to Embodiment 16.

Next, using FIG. 19, dental coupling member 1628 for a mouthpiece according to Embodiment 16 of the present invention is described.

Dental coupling member 1628 has rod 34 and cylinder 1630. Cylinder 1630 is formed in a cylindrical shape, being open at the end on first-orientation end region 1630P side and at the end on second-orientation end region 1630Q side. On the inner peripheral surface of cylinder 1630, female screw part 32B (not shown in FIG. 19; see FIG. 3B) is formed, as with inner tube 32 in Embodiment 1.

Also in Embodiment 16, male screw part 34A includes increased diameter part 34E and constant diameter part 34F (FIGS. 4A, 4B, 5, 6, 7A, 7B, 8A, 8B, 8C, 9, 10, 11A, and 11B), or screwing small-pitch part 34G and screwing large-pitch part 34H (FIGS. 12A, 12B, 13, and 14). Thus, large torque is required when male screw part 34A is threaded into and rotated in female screw part 32B, and male screw part 34A is restrained from becoming loose relative to female screw part 32B.

2-17. Embodiment 17

Figure 20A:
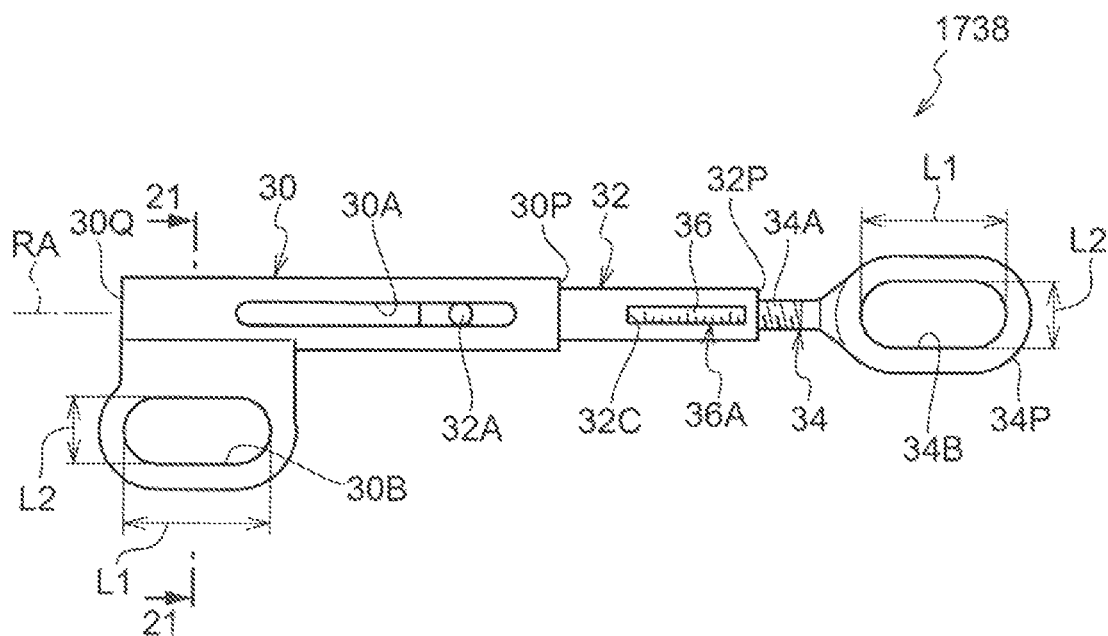
FIG. 20A is a plan view showing the dental coupling member according to Embodiment 17.
Figure 20B:
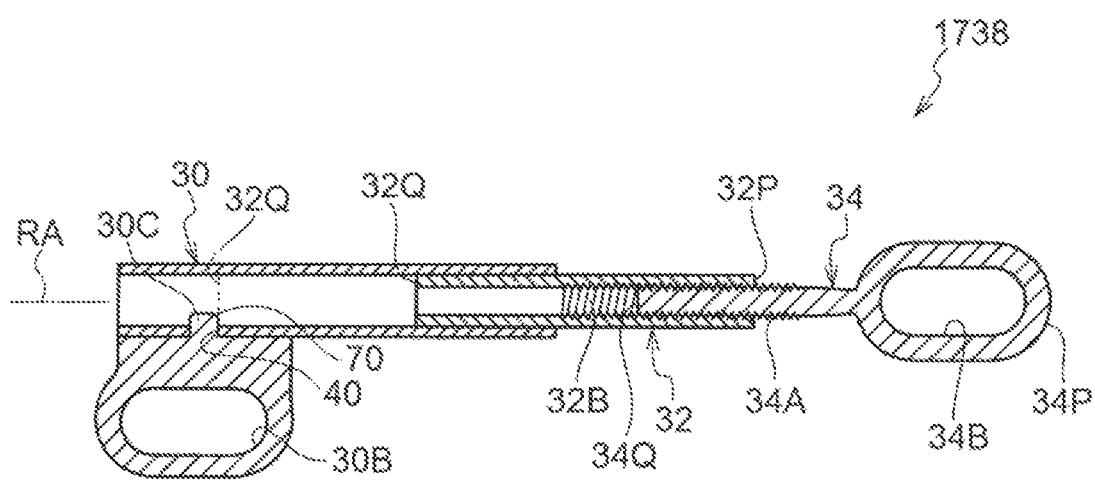
FIG. 20B is a cross-sectional view showing the dental coupling member according to Embodiment 17.

As shown in FIGS. 20A and 20B, dental coupling member 1738 according to Embodiment 17 has outer tube 30 which is a tubular elongated body open at the end on first-orientation end region 30P side and at the end on second-orientation end region 30Q side, inner tube 32 which is a tubular elongated body slidably inserted in outer tube 30, and rod 34 which is an elongated body to be inserted into inner tube 32. Inner tube 32 is an example of "insert".

Figure 21:
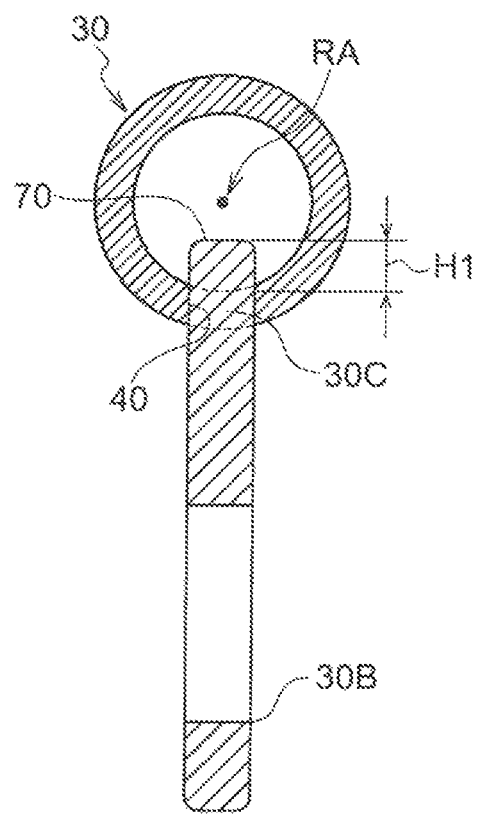
FIG. 21 is a cross-sectional view taken along line 21-21 in FIG. 20A and showing the dental coupling member for a mouthpiece according to Embodiment 17.

Protrusion 70 projects from the inner peripheral surface of outer tube 30. In Embodiment 17, lug 30C projects at the longitudinal center of upper eyelet 30B. As shown in FIG. 21, protrusion 70 is provided at a circumferential part of the inner peripheral surface of outer tube 30.

Through hole 30R into which this lug 30C is inserted is formed in outer tube 30. Upper eyelet 30B is fixed to outer tube 30 by welding, bonding, crimping or the like. Here, upper eyelet 30B is attached to upper attaching part 16 on the outer periphery side of outer tube 30 and is located penetrating through hole 30R such that lug 30C will be protrusion 70 facing the end surface of inner tube 32 on second-orientation end region 32Q side on the inner peripheral surface of outer tube 30. A height H1 of lug 30C is greater than the thickness of outer tube 30. Thus, when fixed, the tip of protrusion 70 projects from the inner peripheral surface of outer tube 30.

Here, the height H1 of protrusion 70 is a height that is not excessively great so that the tip of lug 30C lies off the axial center RA of the inner peripheral surface of outer tube 30, avoiding the axial center RA, as shown in FIG. 21.

The position of protrusion 70 in the axial direction is such a position that limits the movement of inner tube 32 within a predetermined range when it moves in outer tube 30 to second-orientation end region 30Q side by the contact of the end surface of inner tube 32 on second-orientation end region 32Q side with protrusion 70.

In Embodiment 17, the sliding of inner tube 32 to second-orientation end region 30Q side of outer tube 30 is limited within a predetermined range by the hitting of the end surface of inner tube 32 on second-orientation end region 32Q side against protrusion 70, as described later. Specifically, when the mouth is closed, the end surface of inner tube 32 on second-orientation end region 32Q side hits protrusion 70 at the position indicated by the two-dot chain line in FIG. 20B, thus limiting the sliding of inner tube 32 to the side of second-orientation end region 30Q of outer tube 30 to limit the backward movement of mandibular dental appliance 14 on the row of teeth (to the right side in FIG. 20A). Likewise, the sliding of inner tube 32 to the first-orientation end region side is limited within a predetermined range by the hitting of housed part 32A against the end of long hole 30A in outer tube 30 on first-orientation end region 30P side. The distance (center-to-center distance) between upper attaching part 16 and lower attaching part 18 is adjusted between about 18 mm and 50 mm with dental coupling member 1738.

In doing so, housed part 32A of inner tube 32 moves downward from the upper end of long hole 30A of outer tube 30 (to the left in FIG. 20B), where it may or may not abut against the lower end of long hole 30A (the left end in FIG. 20B).

Embodiment 17 also limits the movement of inner tube 32 to second-orientation end region 30Q side of outer tube 30 in a predetermined range by the hitting of the end surface of inner tube 32 on second-orientation end region 32Q side against protrusion 70 projecting from the inner peripheral surface of outer tube 30.

Thus, the structure of outer tube 30 is simple as there is no need to form the inner peripheral surface of outer tube 30 such that the inner diameter changes in two or more steps so as to form a wall and the like to be contacted by inner tube 32. Since no portion where the inner diameter changes is formed on the inner peripheral surface of the outer tube, the structure of outer tube 30 is simple. Outer tube 30 is then easy to shape and the manufacturing cost of outer tube 30 can be reduced.

As shown in FIG. 21, protrusion 70 is formed in a circumferential part of the inner peripheral surface of outer tube 30. Since protrusion 70 is not formed on the entire circumference, the inner diameter of the inner peripheral surface of outer tube 30 is constant and the structures of outer tube 30 and protrusion 70 are simple. In particular, since upper eyelet 30B is provided in a circumferential part of outer tube 30, a structure with protrusion 70 can be produced by forming lug 30C on this upper eyelet 30B.

Protrusion 70 has a height H1 that does not reach the axial center RA inside outer tube 30. Thus, protrusion 70 will not hinder when a tool or the like is inserted from the second-orientation end region 30Q side of outer tube 30, facilitating the insertion of the tool or the like.

Housed part 32A of inner tube 32 is housed such that it can move only in the axial direction within long hole 30A of outer tube 30. Thus, when inner tube 32 slides in outer tube 30, inner tube 32 can be restrained from rotating about the axis relative to outer tube 30.

2-18. Embodiment 18

Figure 22:
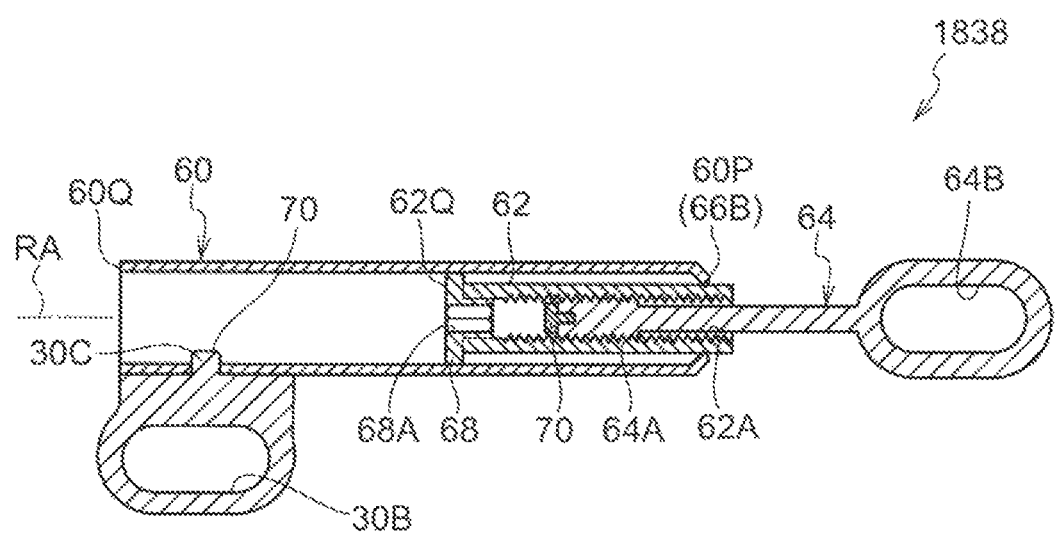
FIG. 22 is a cross-sectional view showing the dental coupling member according to Embodiment 18.

As shown in FIG. 22, dental coupling member 1838 according to Embodiment 18 has tubular outer tube 60 open at the end on first-orientation end region 60P side and at the end on second-orientation end region 60Q side, tubular inner tube 62 slidably provided in outer tube 60, and rod 64 to be engaged with inner tube 62.

In first-orientation end region 60P of outer tube 60, decreased diameter part 66B having a smaller diameter than that of the other portion of outer tube 60 is formed. This decreased diameter part 66B is formed by crimping first-orientation end region 60P of outer tube 60, for example. While such a decreased diameter part 66B is formed in the first-orientation end region of outer tube 60, the inner diameter of the inner peripheral surface of outer tube 60 is constant. Decreased diameter part 66B is an example of "limiting part".

In second-orientation end region 62Q of inner tube 62, increased diameter part 68 with a larger outer diameter than the outer diameter of the other portion of inner tube 62 is integrally formed. Increased diameter part 68 of inner tube 62 faces protrusion 70 of outer tube 60 on second-orientation end region 60Q side, and its end surface on first-orientation end region 60P side faces decreased diameter part 66B. Increased diameter part 68 accordingly can slide within the range between protrusion 70 and decreased diameter part 66B. Here, it may be any portion of inner tube 62 that faces decreased diameter part 66B; it does not have to be increased diameter part 68, that is, a portion with an increased outer diameter.

Insertion groove 68A is formed in the center of the end surface of increased diameter part 68 in second-orientation end region 62Q of inner tube 62. Insertion groove 68A is hexagonal, allowing insertion of a tool such as a hexagonal wrench.

On Rod 64, male screw part 64A formed in the second-orientation end region has been screwed with female screw part 62A formed on the inner peripheral surface of inner tube 62. Abutting part 62E is provided on the end surface of rod 64 on the second-orientation end region side. Abutting part 62E faces the end surface of increased diameter part 68 on the first-orientation end region side.

Dental coupling member 1838 is adjustable in length by sliding of inner tube 62 in outer tube 60. In doing so, the movement of inner tube 62 to the second-orientation end region side is limited within a certain range by increased diameter part 68 of inner tube 62 hitting protrusion 70. Likewise, the movement of inner tube 62 to the first-orientation end region side is limited by increased diameter part 68 of inner tube 62 hitting decreased diameter part 66B.

To adjust the position of rod 64 relative to inner tube 62, a tool such as a hexagonal wrench is inserted into insertion groove 68A in increased diameter part 68 of inner tube 62 from the open end of outer tube 60 on second-orientation end region 60Q side. The hexagonal wrench is then rotated about the axis to cause inner tube 62 to rotate about the axis, thereby adjusting the amount of screwing of male screw part 64A of rod 64 into female screw part 62A of inner tube 62. Since protrusion 70 avoids the axial center RA of the inner peripheral surface of outer tube 60 and lies off the axial center RA, the shaft of a hexagonal wrench and the like can be easily inserted.

Embodiment 18 limits the movement of inner tube 62 to the second-orientation end region side by means of protrusion 70 on the inner peripheral surface of outer tube 60.

Thus, the structure is simple because there is no need to form a part where the inner diameter changes (such as a wall) on the inner peripheral surface of outer tube 60 and thus the inner diameter of the inner peripheral surface of outer tube 60 is constant. Outer tube 60 is easy to shape, which can contribute to reduction in the manufacturing cost of outer tube 60.

Additionally, Embodiment 18 allows the axial position of rod 64 relative to inner tube 62 to be adjusted by rotating inner tube 62 about the axis, without rotation of rod 34 about the axis. Thus, the length of dental coupling member 1838 can be easily adjusted with lower eyelet 64B of rod 64 remaining engaged with flange 26 in FIG. 1.

2-19. Embodiment 19

Figure 23:
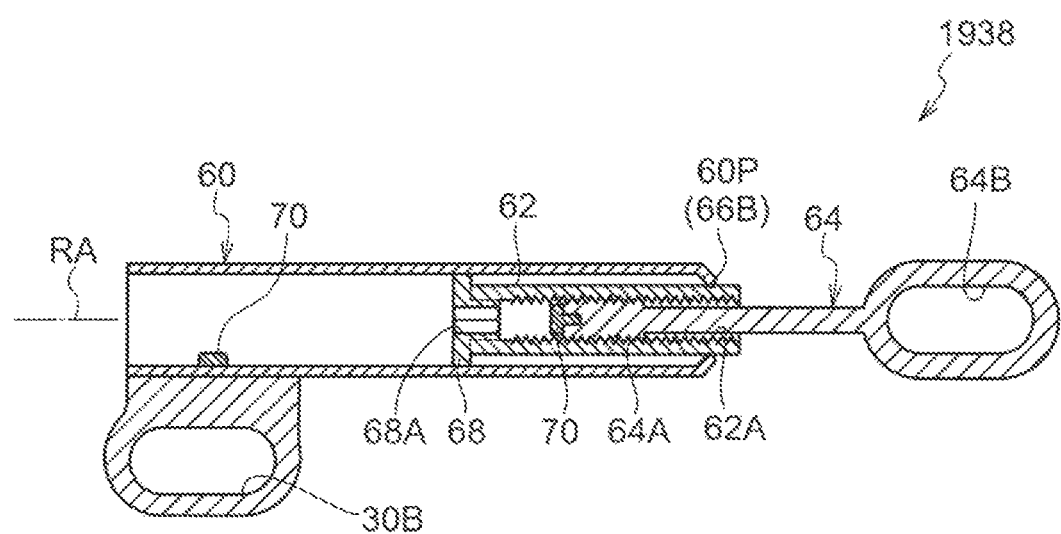
FIG. 23 is a cross-sectional view showing the dental coupling member according to Embodiment 19.

As shown in FIG. 23, in dental coupling member 1938 according to Embodiment 19, upper eyelet 30B does not have lug 30C (see FIG. 20B), and upper eyelet 30B and protrusion 70 are separate components. Protrusion 70 is fixed to the inner peripheral surface of outer tube 60 by welding, bonding and the like.

Because upper eyelet 30B and protrusion 70 in Embodiment 19 are separate components as described above, it provides high degree of freedom in the position where protrusion 70 is provided. Additionally, as outer tube 60 has no through hole 30R (see FIG. 20B) formed therein, the shaping of outer tube 60 is even easier.

As opposed to Embodiment 19 as described above, a structure with protrusion 70 provided on upper eyelet 30B (Embodiment 17 or 18, for example) does not incur an increase in the number of parts because upper eyelet 30B and protrusion 70 are an integral piece. Moreover, by inserting lug 30C (see FIGS. 20B and 21) into through hole 30R, a structure with protrusion 70 projecting from the inner peripheral surface of outer tube 30 can be easily produced. Formation can be done by fixing upper eyelet 30B to outer tube 30, 60 and at the same time reliably positioning protrusion 70 relative to outer tube 30, 60.

In Embodiments 17 through 19, protrusion 70 is provided in a circumferential part of the inner peripheral surface of outer tube 30, 60. As protrusion 70 is not provided on the entire circumference of the inner peripheral surface of outer tube 30, 60, the structure of protrusion 70 can be simplified.

Of course, it is not intended to exclude a structure with protrusion 70 provided on the entire circumference of the inner peripheral surface of outer tube 30, 60.

3. Other Variations

The present invention is not limited to what is described above but various other embodiments are possible within the scope of the idea of the present invention.

For example, as described above, mouthpiece 10, when not worn on the row of teeth, permits attachment and detachment of upper eyelet 30B and lower eyelet 34B to/from flanges 22, 26 of upper attaching part 16 and lower attaching part 18.

However, upper eyelet 30B and lower eyelet 34B may be attached to flanges 22, 26 in an undetachable manner such as by bonding or screwing. Further, the shapes of flange 22, 26, upper eyelet 30B, and lower eyelet 34B are not limited to corner-rounded rectangular shapes but may be any shape such as a perfect circle.

While upper eyelet 30B was described above as being formed at a position offset from the axial center of outer tube 30, it may be formed on the axial center of outer tube 30. Further, a configuration is also possible that allows the amount of screwing of male screw part 34A to be checked by viewing the position of the upper end of male screw part 34A from opening 32C of inner tube 32, instead of forming scale 36A on rod 34.

In Embodiment 15, decreased diameter part 66A is formed by increasing the thickness of outer tube 60 and decreased diameter part 66B is formed by crimping the lower end of outer tube 60. However, the methods of forming decreased diameter parts 66A, 66B are not limited to the above embodiment; decreased diameter parts 66A, 66B may be formed in the same method. Also, while increased diameter part 68 was described as being formed integrally with inner tube 62, increased diameter part 68 as a separate member may be joined with second-orientation end region 62Q of inner tube 62.

In Embodiments 17 through 19, the structure of protrusion 70 can be simplified because protrusion 70 is provided in a circumferential part of the inner peripheral surface of outer tube 30, 60 and protrusion 70 is not provided on the entire circumference of the inner peripheral surface of outer tube 30, 60. However, it is not intended to exclude a structure with protrusion 70 provided on the entire circumference of the inner peripheral surface of outer tube 30, 60.

In Embodiments 18 and 19, decreased diameter part 66B is formed by crimping the lower end of outer tube 60. However, the method of forming decreased diameter part 66B is not limited to the above embodiment. Additionally, while increased diameter part 68 was described as being formed integrally with inner tube 62, increased diameter part 68 as a separate member may be joined with second-orientation end region 62Q of inner tube 62.

Further, in Embodiments 1 through 15 and 17 through 19, rod 34, 44, 54, 64 with male screw part 34A, 44A, 54A, 64A formed thereon serves as the first elongated body having a screwing part, and inner tube 32, 42, 52, 62 and outer tube 30, 40, 50, 60 serve as the second elongated body having a screwed part, with female screw part 32B, 42A, 52A, 62A formed on inner tube 32, 42, 52, 62. However, a structure is also possible where rod 34, 44, 54, 64 with a female screw part formed thereon serves as the second elongated body having a screwed part, and inner tube 32, 42, 52, 62 and outer tube 30, 40, 50, 60 serve as the first elongated body having a screwing part, with male screw part formed on inner tube 32, 42, 52, 62. In such a case, rod 34, 44, 54, 64 may be a tubular member instead of a solid columnar member, and inner tube 32, 42, 52, 62 may be a solid columnar member instead of a tubular member.

Similarly, in Embodiment 16, rod 34 with male screw part 34A formed thereon serves as the first elongated body having a screwing part, and cylinder 1630 with female screw part 32B formed thereon serves as the second elongated body having a screwed part. However, a structure is also possible where rod 34 with a female screw part formed thereon serves as the second elongated body having a screwed part and cylinder 1630 with a male screw part formed thereon serves as the first elongated body having a screwing part. In such a case, rod 34 may be a tubular member instead of a solid columnar member, and cylinder 1630 may be a solid columnar member instead of a tubular member.

Further, in Embodiments 17 through 19, rod 34, 64 with male screw part 34A, 64A formed thereon serves as the first elongated body having a screwing part, and inner tube 32, 62 with female screw part 32B, 62A formed thereon serves as a third elongated body having a screwed part. However, a structure is also possible where rod 34, 64 with a female screw part formed thereon serves as the third elongated body having a screwed part, and inner tube 32, 62 and outer tube 30, 60 serve as the first elongated body having a screwing part, with a male screw part formed on inner tube 32, 62. In such a case, inner tube 32, 62 as an insert does not have to be a tubular member but may be a solid columnar member.

Although rod 34, 44, 54, 64 is a solid columnar member in Embodiments 1 through 19 (see FIGS. 3B, 16, 17, 18, 20B, 22, and 23), rod 34, 44, 54, 64 may be a hollow cylinder. Making rod 34, 44, 54, 64 a hollow cylinder can reduce the weight of the dental coupling member.

In Embodiments 1 through 4, the male screw part should have at least two distinct outer diameters; for example, it may be of a structure with three or more distinct outer diameters. A male screw part with three or more distinct outer diameters also generates large frictional resistance during rotation because a portion with a larger outer diameter makes strong contact with the female screw part when the male screw part is screwed with the female screw part. A male screw part (screwing part) structured with multiple large diameter parts and a small diameter part is also possible.

In Embodiments 1 through 8, there should be at least two distinct clearances between the screwing part (the male screw part is an example of the same) and the screwed part (the female screw part is an example of the same) with formation of different-diameter part(s) on either one or both of the screwing part and the screwed part. For example, a structure is also possible where the screwing part has a changing outer diameter and the screwed part has a changing inner diameter, so that they have at least two distinct clearances between them.

In Embodiments 9 through 12, there should be at least two distinct pitch differences between the screwing part (the male screw part is an example of the same) and the screwed part (the female screw part is an example of the same) with formation of different-pitch part(s) on either one or both of the screwing part and the screwed part. For example, a structure is also possible where both the screwing part and the screwed part may change pitches, so that they have at least two distinct pitch differences between them.

In Embodiments 17 through 19, either one or both of the male screw part and the female is provided with a different-torque part that involves a different torque for screwing with the other of the male screw part and the female screw part so as to form a part with larger frictional force, thus restraining the loosening of the male screw part relative to the female screw part even after torque has been released, like in Embodiments 1 through 12.

Additionally, materials to form maxillary dental appliance 12, mandibular dental appliance 14, upper attaching part 16, lower attaching part 18, and dental coupling member 28 are not limited to those materials mentioned in the above embodiments. For example, although upper attaching part 16, lower attaching part 18, and dental coupling member 28 were described as being made of metal, they may be made of plastic in terms of applicability to patients with metal allergy, reduction in weight with the component strength retained, or relief of discomfort in the mouth.

While a mouthpiece was referred to above as an example of an appliance using dental coupling members, an appliance using dental coupling members may also be an orthodontic appliance, for example. An orthodontic appliance includes a lower-teeth attachment to be attached to lower teeth for orthodontically correcting a row of teeth and an upper-teeth attachment to be attached to upper teeth for orthodontically correcting a row of teeth. These lower- and upper-teeth attachments include expanders, wires or the like for orthodontically correcting a row of teeth. Further, the lower-teeth attachment has a first attaching part and the upper-teeth attachment has a second attaching part. Then, by coupling the dental coupling appliance according to any of the above-described embodiments with the first attaching part of the lower-teeth attachment and the second attaching part of the upper-teeth attachment, the dental coupling appliance is located between the lower-teeth attachment and the upper-teeth attachment such that the dental coupling appliance couples the lower-teeth attachment and the upper-teeth attachment with each other.

[Exemplary Configurations of Dental Coupling Members, Mouthpieces, and Dental Appliances]

According to Embodiments 1 through 16, a dental coupling member is provided, including:

a first elongated body having, in a first-orientation end region, a first coupling part to be coupled with a first attaching part of a first dental appliance and having a screwing part in a second-orientation end region; and a second elongated body having, in a second-orientation end region, a second coupling part to be coupled with a second attaching part of a second dental appliance and having, on an inner peripheral surface of the first-orientation end region, a screwed part with which the screwing part is screwed, in which the dental coupling member includes, on either one or both of the screwing part and the screwed part, a different-torque part that involves a different torque for screwing with the other of the screwing part and the screwed part.

This dental coupling member maintains the relative positions of members by restraining screws from loosening, making it easy to maintain the relative positions of two dental appliances worn on the row of teeth on the upper or lower jaw.

According to Embodiments 1 through 8, in the dental coupling member set forth above, the different-torque part is a different-diameter part that gives at least two distinct lengths of radial clearance between the screwing part and the screwed part.

This dental coupling member has a different-diameter part that gives at least two distinct lengths of radial clearance between the screwing part and the screwed part. Of the different-diameter part, in a portion with a narrower clearance, the screwing part and the screwed part tend to make stronger contact with each other and frictional force is large compared to a portion with a wider clearance, so loosening between the screwing part and the screwed part can be restrained. At the same time, of the different-diameter part, the screwing part is screwed with the screwed part also in the portion where the radial clearance between the screwing part and the screwed part is wide. Thus, the force that acts in the state of being screwed with the screwed part is distributed in the screwing part as a whole.

According to Embodiments 1 through 7, in the dental coupling member set forth above, the different-diameter part is provided in the screwing part, and the screwing part includes:

a small diameter part to be screwed with the screwed part; and a large diameter part which has a larger outer diameter than an outer diameter of the small diameter part and is to be screwed with the screwed part.

By providing the screwing part with a small diameter part having a relatively small outer diameter and a large diameter part having a relatively large outer diameter, this dental coupling member can produce a screwing part structured with at least two distinct outer diameters.

According to Embodiments 1 through 4, in the dental coupling member set forth above, the large diameter part is formed by the screwing part being partially segmented by a gap part of the first elongated body and spread outward.

With this dental coupling member, the first elongated body has a gap part and the large diameter part can be elastically deformed inward in the radial direction of the first elongated body such that this gap part is decreased. That is, since the large diameter part is screwed with the screwed part while undergoing elastic deformation, load can be made to act from the large diameter part to the screwed part while restraining the abrasion of the large diameter part.

According to Embodiment 1, in the dental coupling member set forth above, the gap part is a slit extending from an axial center of the first elongated body toward an outer periphery so as to segment the screwing part.

This dental coupling member is easy to form because the gap part is a slit.

According to Embodiment 2, in the dental coupling member set forth above, the gap part is a slit that segments the screwing part into three or more parts.

With this dental coupling member, the large diameter part can be segmented into three or more parts in the circumferential direction of the first elongated body. A large diameter part with such segmentation is easy to elastically deform and facilitates the insertion of a screw.

According to Embodiment 3, in the dental coupling member set forth above, the gap part is a slit that segments the screwing part into a portion including the axial center of the first elongated body and a portion not including the axial center of the first elongated body.

Since the large diameter part is segmented into multiple portions of different shapes, this dental coupling member permits adjustment of the elasticity of the segmented parts and also permits adjustment of frictional force when the screwing part is screwed with the screwed part.

According to Embodiment 4, in the dental coupling member set forth above, the gap part is a slit having a shape with a width dimension changing in depth direction.

This dental coupling member makes frictional force against the screwed part act evenly in the segmented parts, while enabling formation of a wider portion with large frictional force against the screwed part.

According to Embodiment 6, in the dental coupling member set forth above, the large diameter part has a cylindrical shape with the outer diameter thereof being constant in the axial direction of the first elongated body.

In this dental coupling member, a portion where the screwing part and the screwed part make strong contact with each other is present in a certain range in the axial direction of the first elongated body. Thus, a portion that generates large frictional force when screwing the screwing part and the screwed part together can be secured to be wide.

According to Embodiment 5, in the dental coupling member set forth above, the large diameter part has a truncated cone shape with the outer diameter thereof increasing toward the second-orientation end region side of the first elongated body.

This dental coupling member can restrain the occurrence of local stress on the screwing large-diameter part because the outer diameter of the screwing large-diameter part does not steeply change.

According to Embodiments 5 and 7, in the dental coupling member set forth above,
the different-diameter part is provided in the screwing part, and
the screwing part has a truncated cone shape or barrel shape with the outer diameter thereof changing throughout the first elongated body in the axial direction.

This dental coupling member enables construction of portions with different lengths of radial clearance between the screwing part and the screwed part over a wide range on the screwing part in the axial direction.

According to Embodiments 5 and 6,
in the dental coupling member set forth above, the different-diameter part has a shape being rotationally symmetric relative to the axial center of the first elongated body.

This dental coupling member restrains radially-biased contact between the screwing part and the screwed part.

According to Embodiments 1 through 7, in the above recited dental coupling member, the inner diameter of the screwed part is constant in the axial direction of the second elongated body.

This dental coupling member facilitates the formation of the screwed part.

According to Embodiments 1 through 7, in the dental coupling member set forth above, the different-diameter part is located on the second-orientation end region side of the screwing part.

This dental coupling member produces a state with large frictional force from an early stage of screwing the screwing part with the screwed part and can restrain the loosening between the screwing part and the screwed part.

According to Embodiments 1 through 7, a dental coupling member is provided, including:
a first elongated body including, in the first-orientation end region, a first coupling part to be coupled with a first attaching part of a first dental appliance and having a screwing part with at least two distinct outer diameters formed in a second-orientation end region; and
a second elongated body including, in a second-orientation end region, a second coupling part to be coupled with a second attaching part of a second dental appliance and having a screwed part formed on an inner peripheral surface of the first-orientation end region, the screwed part being for screwing with the screwing part.

This dental coupling member has a different-diameter part that gives at least two distinct lengths of radial clearance between the screwing part and the screwed part. Of the different-diameter part, in a portion with a narrower clearance, the screwing part and the screwed part tend to make strong contact with each other and frictional force is large compared to a portion with a wider clearance, so loosening between the screwing part and the screwed part can be restrained. At the same time, of the different-diameter part, the screwing part is screwed with the screwed part also in the portion with a wider radial clearance between the screwing part and the screwed part, so that the force that acts in the state of being screwed with the screwed part is distributed in the screwing part as a whole.

According to Embodiments 9 through 12, in the dental coupling member set forth above, the different-torque part is a different-pitch part that gives at least two distinct pitch differences in screwing between the screwing part and the screwed part.

This dental coupling member can restrain loosening between the screwing part and the screwed part because in the different-pitch part, namely a portion with a smaller or larger pitch, the screwing part and the screwed part tend to make strong contact with each other and frictional force is large compared to a portion with the standard pitch of the screwing part and the screwed part. Additionally, since the screwing part is screwed with the screwed part also in the portion with the standard pitch of the screwing part and the screwed part, the force that acts in the state of being screwed with the screwed part is distributed in the screwing part as a whole.

According to Embodiments 9 through 11, in the dental coupling member set forth above,
the different-pitch part is the screwing part, and
the screwing part includes:
a screwing large-pitch part to be screwed with the screwed part; and
a screwing small-pitch part which has a smaller pitch than a pitch of the screwing large-pitch part and is to be screwed with the screwed part.

By providing the screwing part with the screwing large-pitch part having a relatively large pitch and the screwing small-pitch part having a relatively small pitch, this dental coupling member can produce a structure with pitch clearance of at least two distinct lengths between the screwing part and the screwed part.

According to Embodiments 9 through 11, in the dental coupling member set forth above, the screwing part has the screwing small-pitch part in the second-orientation end region.

This dental coupling member produces a state with large frictional force from an early stage of screwing the screwing part with the screwed part and can restrain the loosening between the screwing part and the screwed part.

According to Embodiment 10, in the dental coupling member set forth above, the pitch of the screwing small-pitch part is constant in the axial direction of the first elongated body.

In this dental coupling member, a portion where the screwing part and the screwed part make strong contact with each other is present in a certain range in the axial direction of the first elongated body. Thus, a portion that generates large frictional force when screwing the screwing part and the screwed part together can be secured to be wide.

According to Embodiment 9, in the dental coupling member set forth above, the pitch of the screwing small-pitch part decreases toward the second-orientation end region side of the first elongated body.

This dental coupling member can restrain the occurrence of local stress on the screwing small-pitch part because the pitch of the screwing small-pitch part does not steeply change.

According to Embodiment 9, in the dental coupling member set forth above, the different-pitch part is the screwing part, and the pitch of the screwing part changes throughout the first elongated body in the axial direction.

This dental coupling member enables construction of portions different in the pitch length of the screwing part and the screwed part over a wide range on the screwing part in the axial direction.

According to Embodiments 9 through 12, in the dental coupling member set forth above, the different-pitch part has a shape being rotationally symmetric relative to the axial center of the first elongated body.

This dental coupling member restrains radially-biased contact between the screwing part and the screwed part in the different-pitch part.

According to Embodiments 9 through 11, in the dental coupling member set forth above, the pitch of the screwed part is constant in the axial direction of the second elongated body.

This dental coupling member facilitates the formation of the screwed part.

According to Embodiments 1 through 15, in the dental coupling member set forth above, the second elongated body includes:

an outer tube having the second coupling part in the second-orientation end region, and being open at the end on the first-orientation end region side; and an inner tube which has the screwed part on the inner peripheral surface of the first-orientation end region and is inserted into the outer tube in the second-orientation end region.

With the sliding of the inner tube in the outer tube, this dental coupling member allows the dental coupling member to follow the motion of the first dental appliance and the second dental appliance.

According to Embodiments 13 through 15, in the dental coupling member set forth above, the outer tube has a limiting part for limiting sliding of the inner tube in the axial direction.

This dental coupling member limits the sliding of the inner tube in both axial directions by means of the limiting part formed between the opposite axial ends of the outer tube. Moreover, since the inner tube is inserted in the outer tube, the dental coupling member can be made compact in size compared to a configuration providing a member like a nut outside the outer tube.

According to Embodiments 1 through 7, in the dental coupling member set forth above, the inner tube has a protrusion on the outer peripheral surface of the second-orientation end region, and the outer tube has a long hole as the limiting part which is located on the outer peripheral surface along the axial direction and abuts against the protrusion at its ends to limit the sliding of the inner tube in the axial direction.

This dental coupling member limits the sliding of the inner tube by the abutment of the protrusion formed on the outer peripheral surface of the inner tube against the opposite ends of the long hole formed in the outer peripheral surface of the outer tube. In doing so, the protrusion of the inner tube moves in the long hole of the outer tube, so that the dental coupling member can follow the motion of the first dental appliance and the second dental appliance while restraining the inner tube from rotating about the axis relative to the outer tube.

According to Embodiment 13, in the dental coupling member set forth above, the inner tube has a pair of protrusions facing the outer peripheral surface, and the outer tube has a pair of long holes as the limiting part that are located at opposing positions on the outer peripheral surface and respectively abut against the pair of protrusions at their ends to limit the sliding of the inner tube in the axial direction.

In this dental coupling member, slits into which the protrusions on the inner tube are inserted are formed at opposing positions, respectively, in the outer peripheral surface of the outer tube. Thus, the inner tube can be further restrained from rotating about the axis relative to the outer tube.

According to Embodiment 14, in the dental coupling member set forth above, the outer tube includes a pair of stoppers as the limiting part, the stoppers being provided within the outer tube at a spacing from each other in an axial direction, and the pair of stoppers abut against the inner tube to limit the sliding of the inner tube in the axial direction.

Since this dental coupling member has the inner tube inserted between the pair of stoppers provided inside the outer tube, sliding of the inner tube in both axial directions is limited by the stoppers. As the stoppers are provided inside the outer tube, the dental coupling member can be made compact in size compared to a configuration providing stoppers outside the outer tube.

According to Embodiment 14, in the dental coupling member set forth above, the inner tube has an increased diameter part;

the outer tube has a decreased diameter part as the limiting part, the decreased diameter part having a locally decreased diameter of the inner peripheral surface of the outer tube has; and the decreased diameter part of the outer tube abuts against the increased diameter part of the inner tube to limit the sliding of the inner tube in the axial direction.

This dental coupling member has the decreased diameter part formed on the inner peripheral surface of the outer tube and the increased diameter part formed on the inner tube. Thus, the sliding of the inner tube in both axial directions is limited by the abutment of the increased diameter part of the inner tube against the decreased diameter part of the outer tube. Since the increased diameter part of the inner tube abuts against the decreased diameter part in the outer tube, the dental coupling member can be made compact in size compared to a configuration that makes the increased diameter part of the inner tube abut against the outer tube outside the outer tube.

According to Embodiment 15, in the dental coupling member set forth above, the inner tube is rotated about an axis so as to adjust an amount of screwing of the screwing part of the first elongated body relative to the screwed part of the inner tube.

This dental coupling member allows adjustment to the amount of screwing of the screwing part of the first elongated body relative to the screwed part of the inner tube by rotating the inner tube about the axis, without rotating the first elongated body about the axis. Thus, the length of the dental coupling member can be adjusted with the first-orientation axial end of the first elongated body coupled with the first attaching part.

According to Embodiment 15, in the dental coupling member set forth above, the outer tube has an opening at an end on the second-orientation end region side, and the inner tube has, in the second-orientation end region, an insertion groove into which a tool is to be inserted.

This dental coupling member allows the inner tube to be rotated about the axis by inserting a tool into the insertion groove of the inner tube from the first-orientation axial end of the outer tube and rotating the tool about the axis. This permits adjustment of the position of the first elongated body relative to the inner tube without rotating the first elongated body about the axis. Thus, the length of the dental coupling member can be adjusted with the first elongated body coupled with the first attaching part of the first dental appliance.

According to Embodiments 1 through 19, in the dental coupling member set forth above, the screwing part of the first elongated body is a male screw part with a scale formed thereon, the screwed part of the inner tube is a female screw part, and the inner tube has an opening in an outer peripheral surface of the first-orientation end region, the opening for checking the scale on the first elongated body as inserted into the inner tube.

This dental coupling member allows the length of the dental coupling member to be adjusted by adjusting the amount of screwing of the male screw part of the first elongated body into the female screw part of the inner tube. As a scale is formed on the first elongated body and an opening is formed in the outer peripheral surface at the first-orientation axial end of the inner tube, the amount of screwing of the male screw part into the female screw part can be visually checked by viewing the scale from the opening of the inner tube.

According to Embodiments 17 through 19, a dental coupling member is provided, including:

a first elongated body including, in the first-orientation end region, a first coupling part to be coupled with a first attaching part of a first dental appliance and having a screwing part formed in a second-orientation end region;

an outer tube including, in a second-orientation end region, a second coupling part to be coupled with a second attaching part of a second dental appliance, and being open at an end on the first-orientation end region side;

a third elongated body which has a screwed part formed in the first-orientation end region and is inserted into the outer tube in a second-orientation end region, the screwed part being for screwing with the screwing part; and a protrusion projecting from an inner peripheral surface of the outer tube and facing an end surface of the third elongated body on the second-orientation end region side.

This dental coupling member allows the length of the dental coupling member to be adjusted by adjusting the amount of screwing of the first elongated body into the third elongated body so as to adjust the relative positions of the first dental appliance and the second dental appliance. Also, sliding of the third elongated body in the outer tube enables the dental coupling member to follow the motion of the first dental appliance and the second dental appliance. Additionally, as the protrusion faces the second-orientation axial end of the third elongated body, insertion of the third elongated body can be limited by the sliding of the third elongated body in the outer tube and the second-orientation axial end of the third elongated body making contact with the protrusion. An excessive insertion of the third elongated body can be limited by a simple structure having a protrusion formed on the inner peripheral surface of the outer tube.

According to Embodiments 17 through 19, in the dental coupling member set forth above, the inner diameter of the inner peripheral surface of the outer tube is constant.

Since this dental coupling member has no portions with different diameters on the inner peripheral surface of the outer tube, the structure of the outer tube is simple.

According to Embodiments 17 through 19, in the dental coupling member set forth above, the protrusion is located at a position that projects from a circumferential part on the inner peripheral surface of the outer tube.

Since this dental coupling member does not have the protrusion formed on the entire circumference on the inner peripheral surface of the outer tube, the structures of the outer tube and the protrusion are simple.

According to Embodiments 17 through 19, in the dental coupling member set forth above, the protrusion is located at a position offset from the axial center of the inner peripheral surface of the outer tube.

Since this dental coupling member has the protrusion located at a position offset from the axial center of the inner peripheral surface of the outer tube, the protrusion is compact in size and a tool and the like can be easily inserted from an open part at the first-orientation axial end of the outer tube, compared to a structure with the protrusion reaching the axial center.

According to Embodiments 17 through 19, in the dental coupling member set forth above, the protrusion is integral with the second coupling part.

Since the protrusion is integral with the second coupling part, this dental coupling member involves a small number of parts compared to a structure with the protrusion being separate from the second coupling part.

According to Embodiments 17 through 19, in the dental coupling member set forth above, the outer tube has a through hole therein, and the second coupling part is located penetrating the through hole, is coupled with the second attaching part on the outer periphery side of the outer tube, and the protrusion faces the other surface of the third elongated body on the second-orientation end region side on the inner peripheral surface of the outer tube.

This dental coupling member can produce a structure with the protrusion projecting on the inner peripheral surface of the outer periphery by inserting the protrusion of the second coupling part into the through hole from the outer periphery side of the outer tube. Since the protrusion is inserted into the through hole, the protrusion can be reliably positioned relative to the outer tube.

According to Embodiment 18, in the dental coupling member set forth above, the outer tube has a limiting part for limiting the sliding of the inner tube in the axial direction, and a part of the third elongated body is located between the protrusion and the limiting part.

This dental coupling member limits the movement of the third elongated body to the first-orientation axial end side within a predetermined range.

According to Embodiment 18, in the dental coupling member set forth above, the limiting part is a decreased diameter part where the inner peripheral surface of the outer tube has a decreased diameter.

This dental coupling member can limit the movement of the third elongated body to the first-orientation axial end side within a predetermined range by the contact of the increased diameter part of the third elongated body with the decreased diameter part of the outer tube.

According to Embodiments 17 through 19, in the dental coupling member set forth above, the third elongated body is an inner tube having, on the inner peripheral surface, a screwed part with which the screwing part is screwed.

This dental coupling member allows the screwing part of the first elongated body to be screwed with the screwed part on the inner face of the third elongated body by threading the first elongated body into the third elongated body.

According to Embodiments 17 through 19, in the dental coupling member set forth above, the third elongated body is rotated about the axis so as to adjust the amount of screwing of the screwing part of the first elongated body relative to the screwed part of the third elongated body.

This dental coupling member allows the length of the dental coupling member to be adjusted with the first-orientation axial end of the first elongated body coupled with the first attaching part.

According to Embodiment 18, in the dental coupling member set forth above, the outer tube has an opening at an end on the second-orientation end region side, and the third elongated body has, at the end on the second-orientation end region side, an insertion groove into which a tool is to be inserted.

This dental coupling member allows the third elongated body to be rotated about the axis by inserting a tool into the insertion groove of the third elongated body from the first-orientation axial end of the outer tube and rotating the tool about the axis. This permits adjustment of the position of the first elongated body relative to the third elongated body without rotating the first elongated body about the axis. Thus, the length of the dental coupling member can be adjusted with the first elongated body coupled with the first attaching part of the first dental appliance.

According to Embodiment 17, in the dental coupling member set forth above, the screwing part of the first elongated body is a male screw part with a scale formed thereon, the screwed part of the third elongated body is a female screw part, and the third elongated body has an opening in the outer peripheral surface in the first-orientation end region.

This dental coupling member allows the length of the dental coupling member to be adjusted by adjusting the amount of screwing of the male screw part of the first elongated body into the female screw part of the third elongated body. As a scale is formed on the first elongated body and an opening is formed in the outer peripheral surface at the first-orientation axial end of the third elongated body, the amount of screwing of the male screw part into the female screw part can be visually checked by viewing the scale from the opening of the third elongated body.

According to Embodiments 1 through 19, a mouthpiece is provided, including:

the dental coupling member according to any one of the embodiments above;

a mandibular piece as the first dental appliance; and a maxillary piece as the second dental appliance.

According to Embodiments 1 through 19, an orthodontic appliance is provided, including the dental coupling member according to any one of the embodiments above;

a lower-teeth attachment as the first dental appliance to be attached to lower teeth for orthodontically correcting a row of teeth; and an upper-teeth attachment as the second dental appliance to be attached to upper teeth for orthodontically correcting a row of teeth.

The present application claims priority based on Japanese Patent Application No. 2016-203869 filed on Oct. 17, 2016, Japanese Patent Application No. 2016-218139 filed on Nov. 8, 2016, Japanese Patent Application No. 2016-228731 filed on Nov. 25, 2016, and Japanese Patent Application No. 2016-228732 filed on Nov. 25, 2016, and the contents of these applications described in their respective specifications, claims and accompanying drawings are incorporated herein.

REFERENCE SIGNS LIST

10 Mouthpiece
12 Maxillary dental appliance (second dental appliance)
12A Outer wall surface
14 Mandibular dental appliance (first dental appliance)
14A Outer wall surface
16 Upper attaching part (second attaching part)
18 Lower attaching part (first attaching part)
28 Dental coupling member
29 Cylinder
30 Outer tube
30B Upper eyelet
30C Lug
32 Inner tube
32B Female screw part
32C Opening
34 Rod
34A Male screw part
34B Lower eyelet
34E Increased diameter part (large diameter part)
34F Constant diameter part (small diameter part)
34G Screwing small-pitch part
34H Screwing large-pitch part
40 Outer tube
42 Inner tube
44 Rod
48 Dental coupling member
50 Outer tube
52 Inner tube
52A Female screw part
54 Rod
54A Male screw part
54B Lower eyelet
56A Stopper
56B Stopper
58 Dental coupling member
60 Outer tube
62 Inner tube
62A Female screw part
62E Abutting part
62Q Second-orientation end region
64 Rod
64A Male screw part
64B Lower eyelet
66A, 66B Decreased diameter part
68 Increased diameter part
68A Insertion groove
70 Protrusion
134 Rod
134A Male screw part 134E Increased diameter part
134F Constant diameter part
134Q Second-orientation end region
136 Gap part
234 Rod
234A Male screw part
234E Increased diameter part
234F Constant diameter part
234Q Second-orientation end region
236 Gap part
334 Rod
334A Male screw part
334E Increased diameter part
334F Constant diameter part
334G Small segment
334H Large segment
334Q Second-orientation end region
336 Gap part
434 Rod
434A Male screw part
434E Increased diameter part
434F Constant diameter part
434Q Second-orientation end region
436 Gap part
534 Rod
534A Male screw part
534E Increased diameter part
534F Constant diameter part
534Q Second-orientation end region
634 Rod
634A Male screw part
634E Increased diameter part
634F Constant diameter part
634Q Second-orientation end region
734 Rod
734A Male screw part
734E Increased diameter part
734F Constant diameter part
734Q Second-orientation end region
832 Inner tube
832B Female screw part
832E Inner-diameter reduced part
832Q Second-orientation end region
842 Inner tube
842B Female screw part
842E Inner-diameter reduced part
842Q Second-orientation end region
934 Rod
934A Male screw part
934G Screwing small-pitch part
934H Screwing large-pitch part
934Q Second-orientation end region
1034 Rod
1034A Male screw part
1034G Screwing small-pitch part
1034H Screwing large-pitch part
1034Q Second-orientation end region
1134 Rod
1134A Male screw part
1134G Screwing small-pitch part
1134H Screwing large-pitch part
1134Q Second-orientation end region
1232 Inner tube
1232B Female screw part
1232G Pitch-reduced part
1232P First-orientation end region
1242 Inner tube
1242B Female screw part
1242P First-orientation end region
1338 Dental coupling member
1438 Dental coupling member
1538 Dental coupling member
1628 Dental coupling member
1630 Cylinder
1630P First-orientation end region
1630Q Second-orientation end region
1738 Dental coupling member
1838 Dental coupling member
1938 Dental coupling member

What is claimed is:

1. A dental coupling member, comprising:
a first elongated body including, in a first-orientation end region of the first elongated body, a first coupling part to be coupled with a first attaching part of a first dental appliance and including, in a second-orientation end region, of the first elongated body, a screwing part; and
a second elongated body including, in a second-orientation end region of the second elongated body, a second coupling part to be coupled with a second attaching part of a second dental appliance and including, on an inner peripheral surface of a first-orientation end region of the second elongated body, a screwed part with which the screwing part is screwed,
wherein the dental coupling member further comprises, on either one or both of the screwing part and the screwed part, a different-torque part configured to generate variable torque when screwing with another of the screwing part and the screwed part.

2. The dental coupling member according to claim 1, wherein the different-torque part is a different-diameter part that gives at least two distinct lengths of radial clearance between the screwing part and the screwed part.

3. The dental coupling member according to claim 2, wherein:
the different-diameter part is provided in the screwing part; and
the screwing part includes:
a small diameter part to be screwed with the screwed part; and
a large diameter part which has a larger outer diameter than an outer diameter of the small diameter part and is to be screwed with the screwed part.

4. The dental coupling member according to claim 3, wherein the large diameter part is formed by the screwing part being partially segmented by a gap part of the first elongated body and spread outward.

5. The dental coupling member according to claim 4, wherein the gap part is a slit extending from an axial center of the first elongated body toward an outer periphery so as to segment the screwing part.

6. The dental coupling member according to claim 4, wherein the gap part is a slit having a shape with a width dimension changing in depth direction.

7. The dental coupling member according to claim 1, wherein an inner diameter of the screwed part is constant in an axial direction of the second elongated body.

8. The dental coupling member according to claim 3, wherein the different-diameter part is located on the second-orientation end region side of the screwing part.

9. The dental coupling member according to claim 1, wherein the different-torque part is a different-pitch part that gives at least two distinct pitch differences in screwing between the screwing part and the screwed part.

10. The dental coupling member according to claim 9, wherein:
the different-pitch part is the screwing part; and
the screwing part includes:
a screwing large-pitch part to be screwed with the screwed part; and
a screwing small-pitch part which has a smaller pitch than a pitch of the screwing large-pitch part and is to be screwed with the screwed part.

11. The dental coupling member according to claim 10, wherein the screwing part has the screwing small-pitch part in the second-orientation end region of the first elongated body.

12. The dental coupling member according to claim 1, wherein the second elongated body comprises:
an outer tube having the second coupling part in the second-orientation end region of the outer tube and being open at an end of the first-orientation end region side; and
an inner tube which has the screwed part on an inner peripheral surface of the first-orientation end region of the inner tube and the second-orientation end region of the inner tube is inserted into the outer tube, and
wherein the outer tube includes a limiting part for limiting sliding of the inner tube in an axial direction.

13. The dental coupling member according to claim 12, wherein:
the outer tube includes a pair of stoppers as the limiting part, the stoppers being provided within the outer tube at a spacing from each other in an axial direction, and
the pair of stoppers abut against the inner tube to limit the sliding of the inner tube in the axial direction.

14. The dental coupling member according to claim 12, wherein the inner tube is rotated about an axis so as to adjust an amount of screwing of the screwing part of the first elongated body relative to the screwed part of the inner tube.

15. The dental coupling member according to claim 12, wherein:
the outer tube has an opening at an end on the second-orientation end region side; and
the inner tube has, in the second-orientation end region of the inner tube, an insertion groove into which a tool is to be inserted.

16. The dental coupling member according to claim 12, wherein:
the screwing part of the first elongated body is a male screw part with a scale formed thereon;
the screwed part of the inner tube is a female screw part; and
the inner tube has an opening in an outer peripheral surface of the first-orientation end region of the inner tube, the opening for checking the scale on the first elongated body as inserted into the inner tube.

17. A mouthpiece, comprising:
the dental coupling member according to claim 1;
a mandibular piece as the first dental appliance; and
a maxillary piece as the second dental appliance.

18. An orthodontic appliance, comprising:
the dental coupling member according to claim 1;
a lower-teeth attachment as the first dental appliance to be attached to lower teeth for orthodontically correcting a row of teeth; and
an upper-teeth attachment as the second dental appliance to be attached to upper teeth for orthodontically correcting a row of teeth.

* * * * *